US008666774B1

(12) United States Patent
Gonzales, Jr. et al.

(10) Patent No.: US 8,666,774 B1
(45) Date of Patent: Mar. 4, 2014

(54) SYSTEM AND METHOD FOR GAUGING PERFORMANCE BASED ON ANALYSIS OF HOSPITALIST AND PATIENT INFORMATION

(75) Inventors: Merced Gonzales, Jr., San Antonio, TX (US); Francisco Loya, III, Harlingen, TX (US); Michael Gonzales, McAllen, TX (US)

(73) Assignee: Hospitalists Now, Inc., Austin, TX (US)

(*) Notice: Subject to any disclaimer, the term of this patent is extended or adjusted under 35 U.S.C. 154(b) by 83 days.

(21) Appl. No.: 13/317,094

(22) Filed: Oct. 7, 2011

Related U.S. Application Data

(60) Provisional application No. 61/415,654, filed on Nov. 19, 2010, provisional application No. 61/418,717, filed on Dec. 1, 2010.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ............................................................ 705/2, 3
See application file for complete search history.

(56) References Cited

U.S. PATENT DOCUMENTS

| | | | |
|---|---|---|---|
| 5,307,262 A | 4/1994 | Ertel | |
| 6,850,252 B1 | 2/2005 | Hoffberg | |
| 7,181,017 B1 | 2/2007 | Nagel et al. | |
| 7,587,368 B2 | 9/2009 | Felsher | |
| 7,590,550 B2 | 9/2009 | Schoenberg | |
| 7,617,078 B2 | 11/2009 | Rao et al. | |
| 7,630,986 B1 | 12/2009 | Herz et al. | |
| 7,653,558 B2 | 1/2010 | Schoenberg | |
| 7,672,858 B2 | 3/2010 | Tolan et al. | |
| 7,689,682 B1 | 3/2010 | Eldering et al. | |
| 7,734,477 B2 | 6/2010 | Bellin et al. | |
| 7,765,114 B2 | 7/2010 | Frick | |
| 7,774,215 B2 | 8/2010 | Rosow et al. | |
| 7,788,111 B2 | 8/2010 | Haskell et al. | |
| 7,801,956 B1 | 9/2010 | Cumberbatch et al. | |
| 7,805,377 B2 | 9/2010 | Felsher | |
| 7,813,822 B1 | 10/2010 | Hoffberg | |
| 7,818,183 B2 | 10/2010 | Schoenberg | |
| 7,831,445 B2 | 11/2010 | Reiner | |
| 7,835,928 B2 | 11/2010 | Schoenberg | |
| 7,840,418 B2 | 11/2010 | Schoenberg | |
| 7,848,937 B2 | 12/2010 | Schoenberg | |
| 7,853,456 B2 | 12/2010 | Soto et al. | |
| 7,865,377 B2 | 1/2011 | Schoenberg | |
| 7,890,345 B2 | 2/2011 | Schoenberg | |
| 7,890,351 B2 | 2/2011 | Schoenberg | |
| 7,895,061 B2 | 2/2011 | Schoenberg | |
| 7,912,737 B2 | 3/2011 | Schoenberg | |

(Continued)

*Primary Examiner* — Neal Sereboff
(74) *Attorney, Agent, or Firm* — D. Scott Hemingway; Hemingway & Hansen, LLP

(57) ABSTRACT

The present invention provides solutions to many of the problems face by hospitalist medicine providers by supporting the ability to manage patient workflow, improve physician communication, integrate with hospital information systems, identify and document accurate diagnosis codes and capture professional fee charges. The system and method of the present invention enforces discipline in the clinical decision making process by ensuring proper and specific diagnoses and documentation thereof. This system supports the diagnosis, reports patient progress, enhances continuity of care through enhanced communication and notification throughout the treatment episode with all clinical and operational providers, automates core measure compliance documentation and ensure proper notification of any program specific risk management initiatives.

25 Claims, 20 Drawing Sheets

(56) References Cited

U.S. PATENT DOCUMENTS

| | | |
|---|---|---|
| 7,933,783 B2 | 4/2011 | Schoenberg |
| 7,937,275 B2 | 5/2011 | Schoenberg |
| 7,945,456 B2 | 5/2011 | Schoenberg |
| 7,966,647 B1 | 6/2011 | Igoe et al. |
| 7,970,827 B1 | 6/2011 | Cumberbatch et al. |
| 7,974,714 B2 | 7/2011 | Hoffberg |
| 8,073,708 B1 | 12/2011 | Igoe et al. |
| 8,209,218 B1 * | 6/2012 | Basu et al. ............... 705/7.39 |
| 2003/0050794 A1 | 3/2003 | Keck |
| 2003/0158749 A1 * | 8/2003 | Olchanski et al. ............ 705/2 |
| 2004/0064341 A1 | 4/2004 | Langan et al. |
| 2004/0128163 A1 | 7/2004 | Goodman et al. |
| 2005/0177396 A1 | 8/2005 | Gottlieb et al. |
| 2007/0203750 A1 | 8/2007 | Volcheck |
| 2007/0239484 A1 | 10/2007 | Arond et al. |
| 2008/0133269 A1 | 6/2008 | Ching |
| 2008/0133290 A1 * | 6/2008 | Siegrist et al. ............... 705/7 |
| 2008/0154637 A1 * | 6/2008 | Capelli et al. ................ 705/2 |
| 2008/0154642 A1 | 6/2008 | Marble et al. |
| 2008/0243549 A1 | 10/2008 | Woronka et al. |
| 2008/0294507 A1 * | 11/2008 | Reiner ........................ 705/11 |
| 2009/0012816 A1 | 1/2009 | Cookson et al. |
| 2009/0024414 A1 | 1/2009 | Mansour et al. |
| 2009/0099865 A1 | 4/2009 | Zak et al. |
| 2009/0182580 A1 | 7/2009 | Martin et al. |
| 2009/0281826 A1 | 11/2009 | Zak et al. |
| 2010/0114599 A1 | 5/2010 | Lanning et al. |
| 2010/0169119 A1 | 7/2010 | Hussain |
| 2011/0161857 A1 * | 6/2011 | Kramer ....................... 715/772 |
| 2013/0073306 A1 * | 3/2013 | Shlain et al. ................. 705/2 |

* cited by examiner

New Patient

| | |
|---|---|
| Last Name: | [_____]—603 |
| First Name: | [_____] |
| Middle Name: | [_____] |
| PCN: | [_____] |
| MRN: | [_____] |
| Admit Date: | 1/7/2011 |
| Assigned MD: | merced@hospitalistsnow.com ▾ |
| Referring MD: | [_____]—605 |
| Working Dx: | [_____]—606 |

[cancel]  [submit]

*FIG. 6*  601

| Home | Cases | Search | Referring MD | Reports | Admin | Support | HIN Intranet |

| Quick Entry | Census | MDR Form |

Merced's Census

Hospitalists Hospital ▽

| Last Name | First Name | Room # | LOS | Transfer |
|---|---|---|---|---|
| Anderson | Mike | | 35 Days | ☐ |
| Berlin | Irving | | 241 Days | ☐ |
| Duncan | Deborah | | 170 Days | ☐ |
| Gravelt | Tom | | 18 Days | ☐ |
| Nunez | Rene | | 242 Days | ☐ |
| Quiroz | Frank | | 284 Days | ☐ |
| Rodriguez | Isaac | | 241 Days | ☐ |
| teieioo | 28908488d | | 151 Days | ☐ |
| County | Alex | | 148 Days | ☐ |
| DeAlejandro | Test | | 184 Days | ☐ |
| Seymore | Jane | | 241 Days | ☐ |
| Thomas | John | | 35 Days | ☐ |

705 → Transfer to: [▽]   [transfer]

(Optional) Notes: [ ]

Group Census

| Last Name | First Name | Room # | LOS | Assigned DR | Transfer |
|---|---|---|---|---|---|
| adlfkjak | alifja | | 18 Days | arnold@hospitalistsnow.com | ☐ |
| Anderson | Mike | | 35 Days | merced@hospitalistsnow.com | ☐ |
| Berlin | Irving | | 241 Days | arnold@hospitalistsnow.com | ☐ |
| Doe | John | | 262 Days | merced@hospitalistsnow.com | ☐ |
| Duncan | Deborah | | 170 Days | merced@hospitalistsnow.com | ☐ |
| Gonzales | Mercedes | | 109 Days | arnold@hospitalistsnow.com | ☐ |
| Gravelt | Tom | | 18 Days | merced@hospitalistsnow.com | ☐ |
| Hernandez | Tony | | 241 Days | arnold@hospitalistsnow.com | ☐ |
| Jensen | leslie | | 110 Days | arnold@hospitalistsnow.com | ☐ |
| juarez | aleyda | | 161 Days | arnold@hospitalistsnow.com | ☐ |
| juarez | aj | | 170 Days | arnold@hospitalistsnow.com | ☐ |
| juarez | Tom | | 170 Days | arnold@hospitalistsnow.com | ☐ |
| juarez | Angie | | 267 Days | arnold@hospitalistsnow.com | ☐ |
| Macias | Jessika | | 170 Days | arnold@hospitalistsnow.com | ☐ |
| Martinez | Jose | | 242 Days | arnold@hospitalistsnow.com | ☐ |
| Martinez | Michael | | 242 Days | arnold@hospitalistsnow.com | ☐ |
| Mata | Carlos | | 242 Days | arnold@hospitalistsnow.com | ☐ |
| Nunez | Rene | | 242 Days | merced@hospitalistsnow.com | ☐ |
| Patient | Test | | 170 Days | arnold@hospitalistsnow.com | ☐ |

[refresh data]

Hospitalists Now

| Home | Cases | Search | Census | Quick Entry | Referring MD | MDR Form | Admin | Reports | Support | HIN Intranet |

| Year | Month | Status |
|---|---|---|
| 2010 | 4 | SUBMITTED |
| 2010 | 4 | SUBMITTED |

Medical Director Report Form for the month of: [January ▼] [2011 ▼]

Hospital: [Hospitalists Hospital ▼]

ⓘ Looking for a fish bone?   [save as draft]  [submit]  [refresh]

Hospitalist Staff Review: 805 — Review of hospitalist staff. Report upon each staff member individually. Reports should comment upon verbal and written complaints by hospital regarding staff or staff member's complaints regarding the hospital. Also comment on any awards, patient letters, or other 'pats on the back' of our staff – this also includes challenging diagnoses or situations that deserve special mention.

Group Wins: 805 — Describe important wins for the last month such as new physicians admitting to your service, medical staff leadership votes of confidence.

Meeting Summary: 805 — Summary of previous months meetings: State each meeting attended by the hospitalists and give a quick summary. Give special mention to any hospitalist issues discussed.
- Medical Executive Committee
- Performance Improvement Committee
- Internal Medicine
- Department Meeting
- ED/HM Meeting

CPT Utilization

Facility: St Mark's Medical Center
Doctor: All
1/1/2011 – 1/6/2011

| Charge Date | 93306 | 99223 | 99231 | 99232 | 99233 | 99239 |
|---|---|---|---|---|---|---|
| 1/1/2011 | 0 | 4 | 0 | 4 | 11 | 2 |
| 1/2/2011 | 0 | 2 | 1 | 3 | 11 | 3 |
| 1/3/2011 | 0 | 1 | 0 | 1 | 5 | 3 |
| 1/4/2011 | 0 | 0 | 0 | 0 | 6 | 1 |
| 1/5/2011 | 2 | 1 | 0 | 1 | 4 | 2 |
| 1/6/2011 | 0 | 1 | 1 | 2 | 3 | 0 |
| CPT Cumulative Total | 2 | 9 | 1 | 11 | 40 | 11 |

FIG. 13

Home  Cases  Search  Referring MD  Reports  Admin  Support  HIN Intranet     Welcome Merced! Click here to Logout!

| Census | Admin | Survey Stats |

Your Census at *Hospitalists Hospital*

| Last Name | First Name | Middle Name | MRN | PCN | AdmitDate | Room # | LOS (days) |
|---|---|---|---|---|---|---|---|
| Courty | Alex | | 78900884 | 83895601 | 8/12/2010 | | 148 |
| DeAlejandro | Test | | e3930 | 8838 | 7/7/2010 | | 184 |
| Seymore | Jane | | 88374 | 789484 | 5/11/2010 | | 241 |
| Thomas | Johnn | | M93939 | 8889944 | 12/3/2010 | | 35 |
| adlfkjak | alifja | | 121212 | 121212 | 12/20/2010 | | 18 |
| Anderson | Mike | | H93993 | 99398409 | 12/3/2010 | | 35 |
| Berlin | Irving | | 99485 | 388389 | 5/11/2010 | | 241 |
| Doe | John | | 55443 | 123445 | 4/20/2010 | | 262 |
| Duncan | Deborah | r | 234555 | 939094 | 7/21/2010 | | 170 |
| Gonzales | Mercedes | | 939399940 | 84848995 | 9/20/2010 | | 109 |
| Gravelt | Tom | | 29849 | 39872499 | 12/20/2010 | | 18 |
| Hernandez | Tony | | R34339 | 998H | 5/11/2010 | | 241 |
| Jensen | leslie | | 8903934045 | 499499 | 9/19/2010 | | 110 |

| Home | Cases | Search | Referring MD | Reports | Admin | Support | HIN Intranet | Welcome Merced! Click here to Logout! |

| Census | Admin | Survey Stats |

Manage Questions

Question: _____ ~1505

Type: [General ▽]~1510

Category: ☐ Admit H&P  ☐ Follow-up, PN  ☐ Discharge  ☐ Critical Care  ☐ Extended/Prolonged Care  ☐ Core Measure  ☐ Procedure  ☐ Other
                                                                  1510

[Submit]

Current Questions

Question : On my first encounter with my doctor, he/she treated me with courtesy and respect
Type: General
Category: HP
delete Question: On the day I left the hospital, my doctor explained my condition and my medications to me in manner I could understand.
                                                                                                                                1500

*FIG. 15*

428.21 is a Core Measure for Heart Failure (HF)

EF < 40%  ○ Yes  ○ No

ACE-1 OR AR5 on discharge  ○ Yes  ○ No

Beta Blocker on discharge  ○ Yes  ○ No

Discharge instructions  ○ Yes  ○ No

Smoking Cessation Advice  ○ Yes  ○ No

PATIENT: Test, Test
PCM: 88384123
MRM: 39393123
ADMIT DATA: 1/7/2011

[Cancel] [Submit]

Home  Cases  Search  Referring MD  Reports  Admin  Support  HIN Intranet    Welcome Merced! Click here to Logout!

Full HNI WebApp >> HNI Mobile

[        ] [Search] ~1910

Hospitalists Hospital

Your Census at *Hospitalists Hospital*

| Last Name | First Name | Middle Name | Room # | LOS (days) |
|---|---|---|---|---|
| Anderson ~1920 | Mike | | | 35 |
| Berlin | Irving | | | 241 |
| Duncan | Deborah | r | | 170 |
| Gravelt | Tom | | | 18 |
| Nunez | Rene | | | 242 |
| Quiroz | Frank | | | 284 |
| Rodriguez | Isaac | | | 241 |
| teieioo | 28908488d | w | | 151 |
| Test | Test | Test | | 0 |
| Courty | Alex | | | 148 |
| DeAlejandro | Test | | | 184 |
| Seymore | Jane | | | 241 |
| Thomas | Johnn | | | 35 |

*Note: Patients discharged within 48 hours appear in red.

Home  Cases  Search  Referring MD  Reports  Admin  Support  HIN Intranet  Welcome Merced! Click here to Logout!

Full HNI WebApp > HNI Mobile > Patient

Name: Anderson, Mike  view charges
Facility: Hospitalists Hospital
MRN: H93993
PCN: 99398409
Admit Date: 12/3/2010

Status: ● IP  ○ OP
Admit Type: ● AD  ○ CO  ○ OB
Charge Type: ○ HP  ● FU  ○ DC  ○ CC  ○ DX
E/M-CPT: [99231 SBSQ HOSP CARE PR D 15 MIN - IP 1 ▾]
Procedure: [ ▾]
Charge Assigned MD: [merced@hospitalistsnow.com ▾]
Charge Date: [1/7/2011]

[Submit] [Cancel]

ICD9 Descriptions
1: [PNEUMONIA ORGANISM UNSPECIFIED *486*]
2: [ ]
3: [ ]
4: [ ]
5: [ ]
6: [ ]

...more Dx's

SYSTEM AND METHOD FOR GAUGING PERFORMANCE BASED ON ANALYSIS OF HOSPITALIST AND PATIENT INFORMATION

RELATED APPLICATION DATA

This application is related to Provisional Patent Application Ser. Nos. 61/415,654 filed on Nov. 19, 2010 entitled "Patient Data Record Optimization System and Method," and 61/418,717 filed on Dec. 1, 2010 entitled "Patient Satisfaction Survey Database System and Method, and priority is claimed for this earlier filing under 35 U.S.C. §119(e). The Provisional Patent Application is also incorporated by reference into this utility patent application.

TECHNICAL FIELD OF THE INVENTION

This invention relates to a system and method for capturing, analyzing and reporting hospitalist and patient data, including the ability to gauge performance based on analysis of hospitalists and patient information.

BACKGROUND OF THE INVENTION

"Hospital Medicine" has been defined as a medical specialty dedicated to the delivery of comprehensive medical care to hospitalized patients. Practitioners of hospital medicine include physicians ("hospitalists") and non-physician providers who engage in clinical care, teaching, research, or leadership in the field of general hospital medicine. In addition to their core expertise managing the clinical problems of acutely ill, hospitalized patients, hospital medicine practitioners work to enhance the performance of hospitals and healthcare systems.

Hospitalists strive for this goal by: (1) providing Prompt and complete attention to all patient care needs including diagnosis, treatment, and the performance of medical procedures (within their scope of practice), (2) employing quality and process improvement techniques, (3) supporting collaboration, communication, and coordination with all physicians and healthcare personnel caring for hospitalized patients, (4) transitioning safely patient care within the hospital, and from the hospital to the community, which may include oversight of care in post-acute care facilities, (5) using hospital and healthcare resources efficiently.

"Hospitalist" is the term used for doctors who are specialized in the care of patients in the hospital. Following medical school, hospitalists typically undergo residency training in general internal medicine, general pediatrics, or family practice, but may also receive training in other medical disciplines. Some hospitalists undergo additional post residency training specifically focused on hospital medicine, or acquire other indicators of expertise in the field, such as the Society of Hospital Medicine's Fellowship in Hospital Medicine (FHM) or the American Board of Internal Medicine's Recognition of Focused Practice (RFP) in Hospital Medicine.

Factors favoring this specialization include convenience, efficiency, financial strains on primary care doctors, patient safety, cost-effectiveness for hospitals, and need for more specialized and coordinated care for hospitalized patients. Most hospitalists are board-certified internists (internal medicine physicians) who have undergone the same training as other internal medicine doctors including medical school, residency training, and board certification examination.

Hospitalists usually have chosen not to practice traditional internal medicine due to personal preferences, while some hospitalist physicians are family practice doctors or medical subspecialists who have opted to do hospitalist work such as, intensive care doctors, lung doctors (pulmonologists), or kidney doctors (nephrologists). Hospitalist specialties include:

(1) a Neurohospitalist: Many hospitals, particularly those with dedicated stroke centers, are adding neurohospitalists to their staff. Not only are they able to handle complex cases quickly, but hospitals don't have to pay the pricey fees to bring in a neurologist on call, (2) Surgical Hospitalist (a.k.a. Surgicalist): These hospitalists started out as a solution to overcrowded emergency departments. They were brought in to provide timely surgical consults and get patients into surgery quickly, increasing throughput. But the concept stuck, and many hospitals are adding this position as a part of their staff, (3) OB Hospitalists (a.k.a. Laborists): More hospitals are moving toward using laborists. They're able to oversee a labor until the mother's regular OBGYN can make it to the hospital. And because they can more effectively manage tough labors and deliveries, they can reduce a hospital's C-section rate, and (4) Dermatological Hospitalists: These specialists are integrating themselves back into the inpatient setting after long being a predominately office-based specialty. They can be called upon for a number of cases spanning from adverse drug reactions to stem cell transplant complications.

There are many advantages of hospitalists in the care hospitalized patients. One advantage is that hospitalists' have more expertise in caring for complicated hospitalized patients on a daily basis. They are also more available most of the day in the hospital to meet with family members, able to follow-up on tests, answer nurses' questions, and simply to deal with problems that may arise. In many instances, hospitalists' may see a patient more than once a day to assure that care is going according to plan, and to explain test findings to patients and family members.

Hospitalists also coordinate the care of patients' in hospital, which means they are the physicians that organize the communication between different doctors caring for a patient, and serve as the point of contact for other doctors and nurses for questions, updates, and delineating a comprehensive plan of care. They are also the main physician for family members to contact for updates on a loved one.

Similarly, because hospitalists are in the hospital most of the time, they are able to track test results and order necessary follow-up tests promptly. This is in contrast to the traditional setting where your primary doctor may come to the hospital the next day to follow-up the results and take the next necessary step at that time.

Since the hospitalist's "office" is the hospital, and they are also more familiar with the hospital's policies and activities. Many hospitalists are involved in various hospital committees, and assist in improving important areas such as patient safety, medical error reduction, effective communication between physicians and staff, and cost effective patient care. The main disadvantage of having a hospitalist take care of you in the hospital is that, they may not know your detailed medical history as well as your primary doctor. Another problem is that your primary care doctor may not have access to the details of your hospitalization care (tests, procedures, results, medications, medical plan of action, etc.). These problems have been dealt with to a degree by communication between the primary care doctor and the hospitalist, which usually, and ideally, takes place at least twice during a hospitalization, once upon admission and again prior to discharge from the hospital.

As inpatient cases become more complex, hospitals around the country are likely to add more "hyphenated hospitalists" in the near future. The New York Times Jane Gross puts the spotlight on Hospital Medicine with her recent article: "New Breed of Specialists Signs in for Family Doctor." With patients still largely confused or even ignorant of the role of Hospitalists, Gross' article explains, in lay terms, how hospitalists fit into new models of health care delivery: "Because hospitalists are on top of everything that happens to a patient—from entry through treatment and discharge—they are largely credited with reducing the length of hospital stays by anywhere from 17 to 30 percent, and reducing costs by 13 to 20 percent, according to studies in The Journal of the American Medical Association." This article also states that "As their numbers have grown, from 800 in the 1990s to 30,000 today, medical experts have come to see hospitalists as potential leaders in the transition to the Obama administration's health care reforms, to be phased in by 2014." And, "[u]nder the new legislation, hospitals will be penalized for readmissions, medical errors and inefficient operating systems." and "[a]voidable readmissions are the costliest mistakes for the government and the taxpayer, and they now occur for one in five patients, gobbling $17.4 billion of Medicare's current $102.6 billion budget."

As the demand for Hospitalists continues to grow, issues regarding the quality and thoroughness of hospitalist documentation are becoming increasingly important. Hospitals and hospitalist medicine providers are also finding themselves facing regulations mandating that they provide more timely and consistent documentation. There is a current need for a method and system to efficiently and consistently tracks hospitalist performance and productivity while providing a clinical workflow and communication tool between the provider, provider partners and the hospitals they practice in.

SUMMARY OF THE INVENTION

The present invention provides solutions to many of the problems faced by hospitalist medicine providers by supporting the ability to manage patient workflow, improve physician communication, integrate with hospital information systems, identify and document accurate diagnosis codes and capture professional fee charges. The system and method of the present invention enforces discipline in the clinical decision making process by ensuring proper and specific diagnoses and documentation thereof. This system supports the diagnosis, reports patient progress, enhances continuity of care through enhanced communication and notification throughout the treatment episode with all clinical and operational providers, automates core measure compliance documentation and ensure proper notification of any program specific risk management initiatives.

Additionally, the present invention provides a system that generates tailored, concise and detailed reports that benchmark provider's clinical outcomes and financial performance in a dashboard format. These reports provide hospitals and ancillaries a comprehensive view of each provider's performance. This invention is (but is not limited to) a web-based, active server page (ASP) application that provides real-time demographic, financial and clinical information. A user/provider accesses the system through a standard web browser on a computing device or client connected to the Internet or single or multi-tier network.

BRIEF DESCRIPTION OF THE DRAWINGS

The objects and features of the invention will become more readily understood from the following detailed description and appended claims when read in conjunction with the accompanying drawings in which like numerals represent like elements and in which:

FIG. 4 shows an example of physician home screen page, FIG. 5 shows an example of quick charge entry screen, FIG. 6 shows an example of the manual process of creating a patient record, FIG. 7 shows the patient census and the transfer method, FIG. 8 shows the Medical Director Reporting template page, FIG. 9 shows page showing patient's basic details, FIG. 10 shows the patient's charges, FIG. 11 shows the patients diagnosis history and diagnosis search option, FIG. 13 shows the physician CPT Report and Reporting portal field selector, FIG. 14 shows the patient satisfaction report—patient selection portal page, FIG. 15 shows the patient satisfaction report generation administration portal, FIG. 18 shows the JCAHO & CMS Core Measure Notification worksheet. (Example of Heart Failure), FIG. 19 shows mobile device landing page, FIG. 20 shows mobile device quick charge capture page.

The objects and features of the invention will become more readily understood from the following detailed description and appended claims when read in conjunction with the accompanying drawings in which like numerals represent like element.

DETAILED DESCRIPTION OF THE PREFERRED EMBODIMENTS

The present invention works with multiple hospital information systems (HIS), Electronic Medical Record (EMR) systems, administrative data systems, and financial accounting systems. The present system and method extracts, merges and compiles essential data for hospitalist workflow management, clinical decision making, and physician productivity and financial performance reporting in any time sequence.

Figure 1:
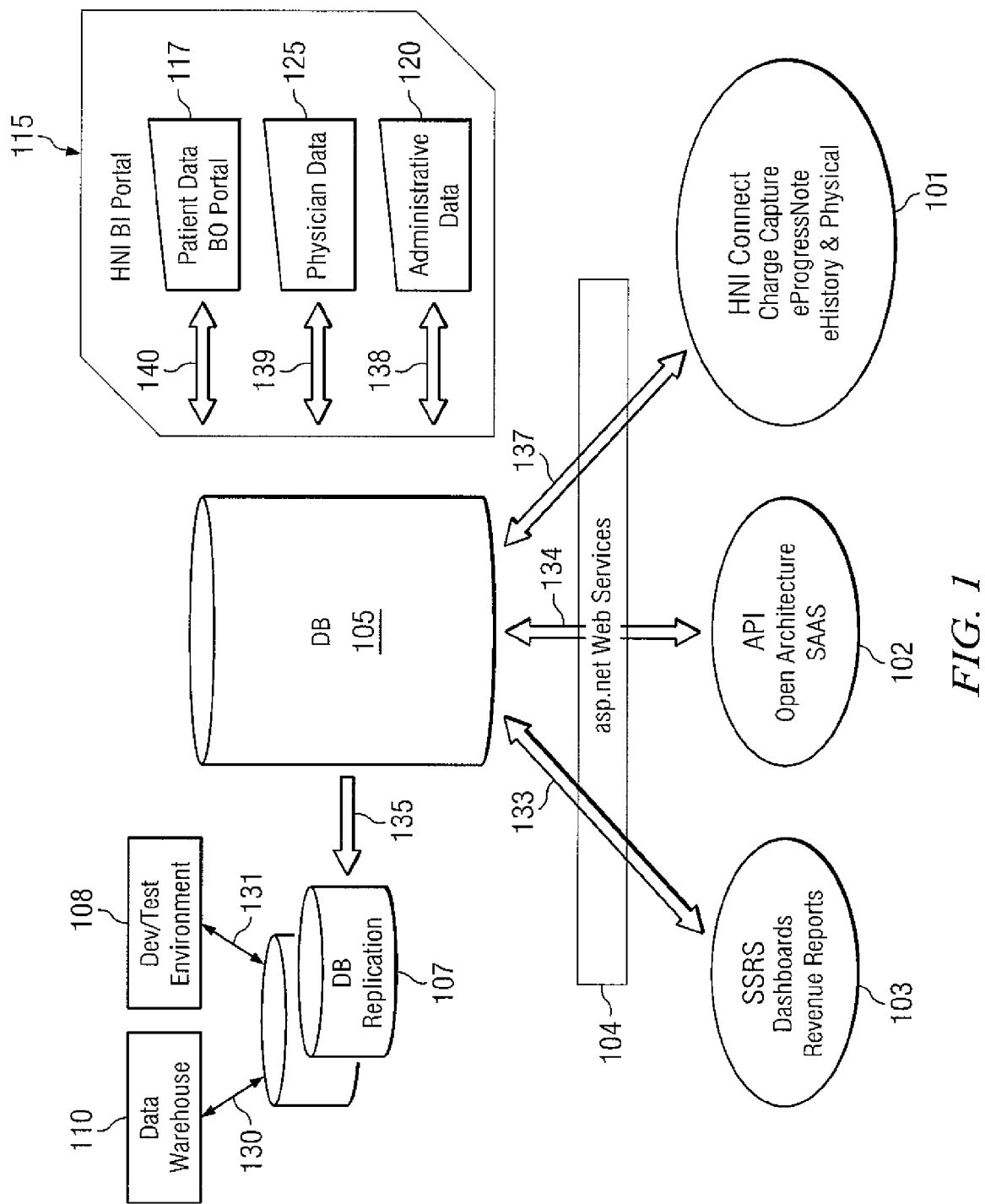
FIG. 1 shows a view of system for hospitalist data in accordance with the present invention.

FIG. 1 shows the architecture and database connections and interaction used in the present invention. The primary database 105 is coupled to a replication database 107 through communication link 135. Replication database 107 is coupled to the data warehouse 110 through communication link 130, and replication database 107 is coupled to development/test environment protocols 108 through communication link 131.

The primary database 105 is coupled to SSRS services protocols 103 through communication link 133 through asp-.net webservices support 104. The SSRS services protocols 103 support the "dashboards" and "revenue report" functions. The primary database 105 is coupled to API services protocols 102 through communication link 134 through asp.net webservices support 104. The API services protocols 102 support the communication with open architecture protocols and SAAS protocols. The API is initialized and runs a specialized program periodically to receive information from a hospital or customer facility. For example, the API code can be executed every 30 minutes to check if any new data has been received from a hospital or customer facility. If data has been received during that period of time, the API program with accumulate the received data and push it into the proper database entries associated with the facility that transferred the data to the computer database software used in the present system. Alternatively, the API subprogram on the system may reach out to certain hospital or customer facilities that provide access to their database system so that the API subprogram can capture data from the hospital or customer facility computer database system for uploading to the data to the computer database software used in the present system.

The data uploaded onto the database 105 is formatted in a normalized manner with baseline data fields that include: visit number (encounter number), medical record number, patient name, diagnosis codes, gender (male/female), age (DOB), admission date, assigned doctor, location/department of facility patient admitted to. The demographic data for the patient is also placed in a normalized format of data fields that include: name of patient (first, middle, last name), visit number, medical record number, date of admission, contact address (home, permanent work or work addresses), insurance information (primary insurer: Medicare, Medicaid, BC/BS, secondary insurer: AFLAC, AARP, tertiary insurer: self, employer), parent/guardian information (if patient is minor), social security number (guarantor and patient). The insurance demographic information includes the policy number, group number, and insurance address for each insurer. Upon admission the baseline and demographic information for that patient is input into the database 105, and the patient information may be accessed from, or input into, the computer system using a desktop computer, mobile phone, intelligent pad devices, or other personal communication device.

The primary database 105 is coupled to HNI Connect services protocols 101 through communication link 137 through asp.net webservices support 104. The HNI Connect services protocols 101 support the invention services for Charge Capture, eProgress Notes, and eHistory & Physical functional protocols. The primary database 105 is coupled to three portals in the HNI B1 Portal 115, with the primary database 105 being coupled to Patient Data BO Portal 117 through communication link 140, and the primary database 105 being coupled to Physician Data 125 protocols through communication link 139, and the primary database 105 also being coupled to Administrative Data protocol 120 through communication link 138.

Figure 2:
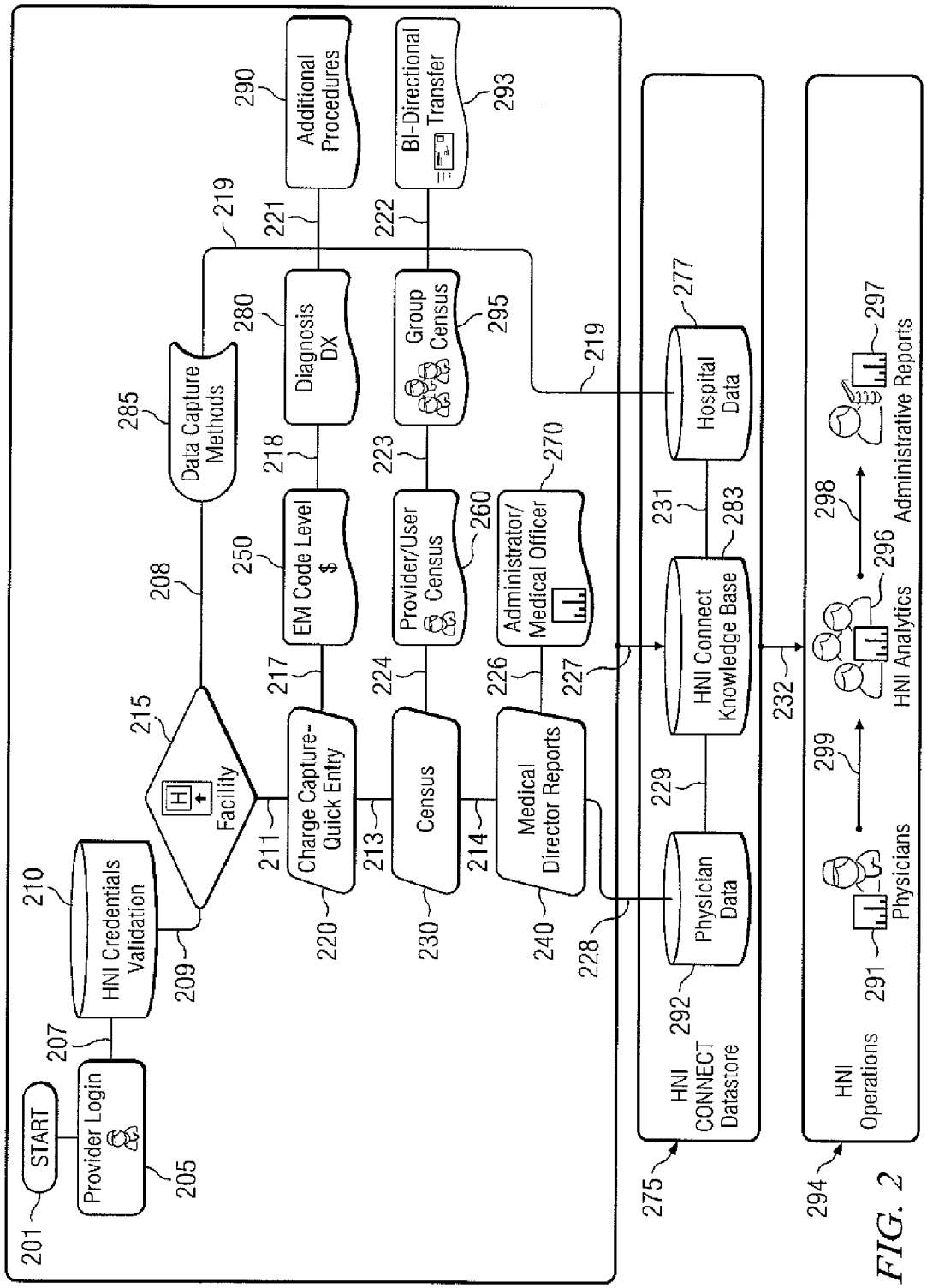
FIG. 2 shows a view of system data architecture for the present invention.

FIG. 2 shows the basic elements of the systems, how it interfaces with external data sources, such as the EMR and HIS systems and data elements associated with inpatient care. Through the present invention's data model, the system enables and integrates data from different types of systems in a seamless, flexible and fast manner. A software control program runs an on demand or by scheduler software routine to check a pre-defined directory that includes data either received or pulled down from different customer hospital systems coupled to the system. The software program starts by asking for a User Login, which must be correctly given to proceed in the program. After the User Login is given to the software program, the software program determines the User's rights and privileges in the next step of the software control program. By rights and privileges, the type of information that defines such rights and privileges includes: (1) the type of user (e.g. doctor, biller, office manager, admin/executive, physical assistant/nurse practitioner, (2) facilities the User has privileges to (e.g. name of facilities, hospitals, etc. where User works or can access information about patients, hospitalists, assistants, etc.), (3) the type of facility that User works at or can access information about patients, hospitalists, assistants, etc. (hospital, long term care, nursing home, assisted living facility, rehabilitation facility, skilled nursing facility, etc.).

After the User's rights and privileges are determined, the software control program proceeds to the Home Screen 101 shown in FIG. 1 where the User can access several options, including the Census sub-program, Charge Capture sub-program, eProgress Notes sub-program, eHistory and Physical subprogram, the Changes sub-program, or the Statistics sub-program (SSRS). From the Home Screen 101 and if the User's rights and privileges permit, the User can access facility-based information including the following: (1) the type of facility that User works at or can access information about patients, hospitalists, assistants, etc. (hospital, long term care, nursing home, assisted living facility, rehabilitation facility, skilled nursing facility, etc.), (2) the identification of the User's patients such as patient name, room location, demographic information (age, primary address, etc.), (3) clinical information for each patient (primary diagnosis). This information may be accessed from, or input into, the computer system using a desktop computer, mobile phone, intelligent pad devices, or other personal communication device.

From the Home Screen 101 and if the User's rights and privileges permit, the User may also input information regarding a patient such as the patient clinical history, diagnosis, treatment(s) received, medications (type and dosage), test results, x-rays or scan results, physical examination records, physician notes, lab results, prescription history. The patient prescription history would include drugs prescribed, dosages prescribed, and frequency of dosage, and this prescription history and present prescription types, amounts, and dosages can be shown graphically in the graphical formats shown in FIG. 16, and the software control program can analyze whether the current prescriptions for a particular patient are comparable to, greater than or less than a metric benchmark for similarly-situated patients.

The patient's physical and clinical history can be input or reviewed on-line using a Patient Data Portal 117, which is controlled by a Patient Data eHistory & Physical subprogram and specialized a graphical user interface (GUI). The patient information regarding the results of initial consults, clinical history reviews, and physicals are input into the computer system using the eHistory & Physical subprogram. Likewise, the progress of the patient can be monitored and updated by the hospitalist using an eProgress Note subprogram shown in the Home Screen 101 of FIG. 1. The information in the Patient Data Portal, Patient Data eHistory & Physical subprogram, and eProgress Note subprogram may be accessed from, or input into, the computer system using a desktop computer, mobile phone, intelligent pad devices, or other personal communication device. The eProgress Note subprogram will provide User feedback while a graphical user interface is completed with the patient progress information, with the feedback giving the doctor, physician, hospitalist or User other queries for information, suggestions on how to complete answers, suggested responses or lists of responses, or other relevant information. Other graphical user interface forms used in other subprograms can also provide the same type of User feedback when the User is providing responsive information to the system subprogram, such as the other queries for information, suggestions on how to complete answers, suggested responses or lists of responses, or other relevant information.

Figure 16:
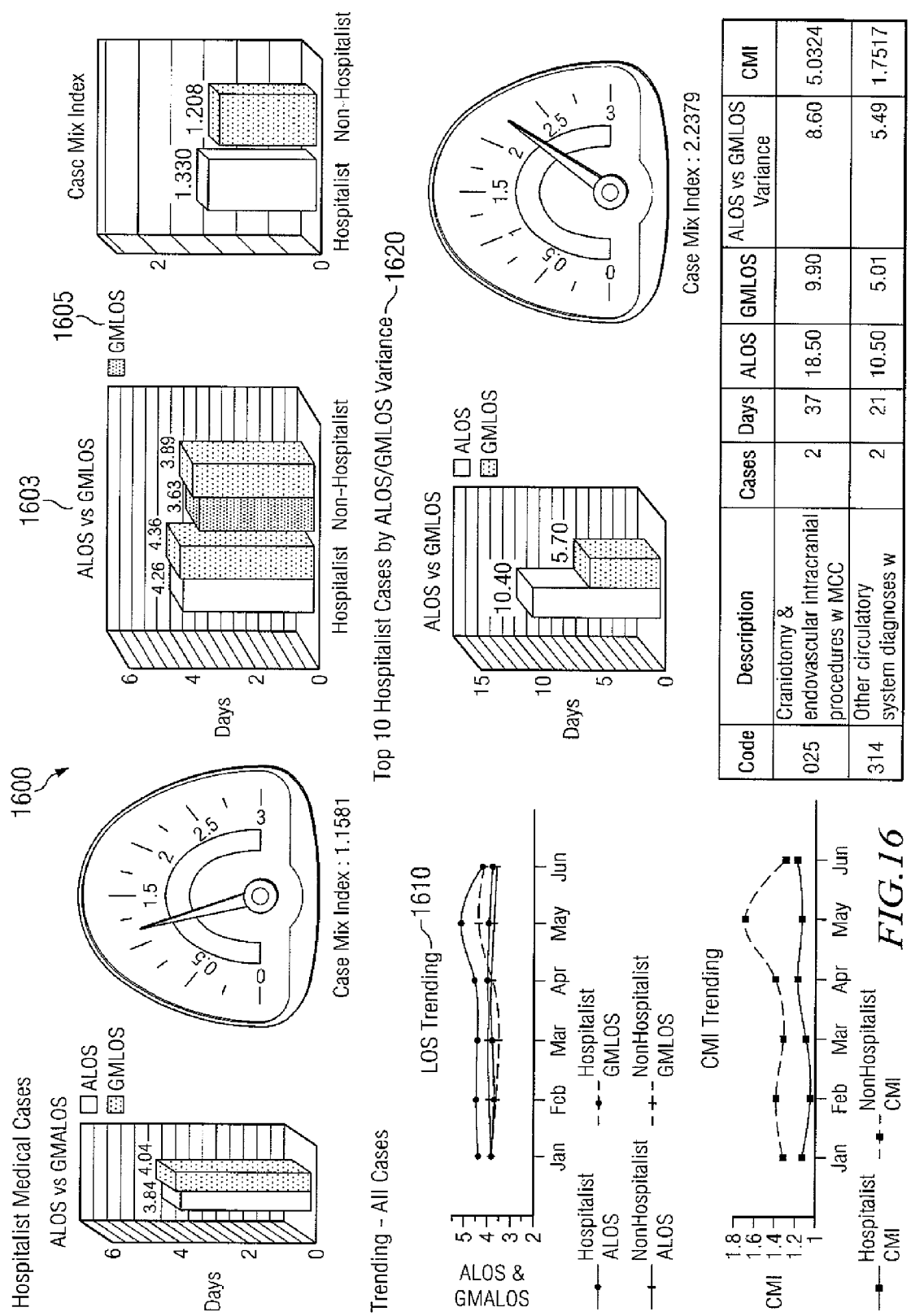
FIG. 16 shows the physician dashboard reporting results.
Figure 17:
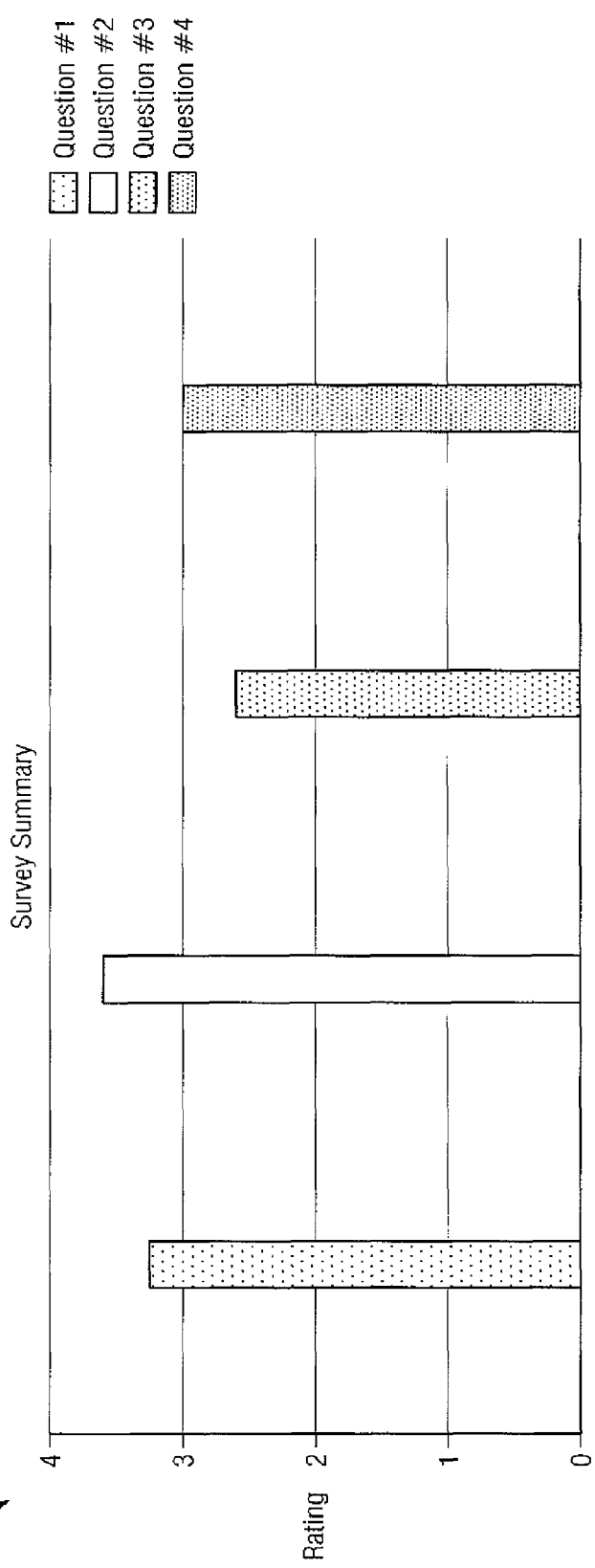
FIG. 17 shows the physician satisfaction report and results.

The User can also access the Statistics subprogram Dashboards, Survey Results and Revenue Reports screens shown in FIGS. 16 and 17 from the Home Screen 101 through the SSRS subprogram screen 103 shown in FIG. 1. The User can also input, modify and access patient information or physician information from the patient and physician subprograms pages, respectively. When the User is permitted to access information for a particular patient, the User can gage patient progress, physical information, treatment administered, or other patient information relating to test results, medication, eProgress Notes, and diagnosis.

The doctor, hospitalist or User can also access Statistics information that will allow him or her to gage their respective workloads compared to other doctors, hospitalists, or Users. The identity of other doctors, hospitalists, or Users may or may not be concealed or hidden from general access to all Users, but the doctor, hospitalist, or User can gage his workload against his co-workers to determine whether he or she is within standards for workload, behind or ahead of co-workers in terms of workload completed, or slower or faster than co-workers in terms of workload completion. The dashboards on FIG. 16 show bar charts, speedometer settings, line charts, and numerical tables so the User can judge his or her performance against a broader metric. By providing this comparative metric information to the User (e.g. comparing performance versus group of other users or other hospitalists), increases in worker productivity are possible, as well as highlighting areas where patient care can be enhanced through the identification of User or physicians that may not be expending sufficient time on particular cases or patients. In addition to gauging relative productivity, the User can also examine his or her individual performances to estimate the fees and wages that may be due to him or her for their work at the facility or with the patient.

All the physician or user information relating to a particular patient can be reviewed with the other physicians or users working with or treating the patient being identified to the User accessing the computer control system, as well as the pertinent information regarding patient progress, physical information, treatment administered, or other patient information relating to test results, medication, eProgress Notes, and diagnosis. The information relating to the Statistics, patient and physician subprograms may be accessed from, or input into, the computer system using a desktop computer, mobile phone, intelligent pad devices, or other personal communication device.

Pre-defined specifications are shared with facility and then software program controls the additional method that takes into account the differences of the hospital data, normalizes to HNI specifications, and populates the appropriate tables and fields in the database. This action occurs either "on demand" or with a scheduler. The workflow process begins as the census is applied to the application. The invention also includes a method to manage workflow for discharged patients. The present invention assimilates demographic, diagnosis code, charge codes, administrative, financial, and clinical data. This embodiment comprises a web-based, active server page (ASP) that provides real-time demographic, financial and clinical information. A user may access the system through any standard web browser operated on a computing device connected to the Internet or other network.

The interactions of the various webpages and protocols in FIG. 2 begin at Start 201 that goes to the Provider Login 205. The Provider Login 205 proceeds to the HNI Credentials Validation 210 at step 207, which then proceeds to the Facility protocol 215 at step 209. The Facility protocol 215 can proceed to the Data Capture protocols 285 at step 208, which is coupled by connection 219 to the Hospital Data database 277 located in the HNI Connect DataStore 275.

The Facility protocol 215 can also proceed to the Charge Capture-Quick Entry protocols 220 by step 211, which will proceed to the EM Code-Level protocol 250 by step 217, which will then proceed to the Diagnosis DX step 280 by step 218, which will then proceed to Additional Procedures protocols 290 by step 221. The Charge Capture-Quick Entry protocols 220 can proceed to the Census protocols 230 by step 213, which will then proceed to the Provider/User Census protocols 260 by step 224, which will then proceed to the Group Census 295 by step 223, which will then proceed to the Bi-Directional Transfer protocols 293 by step 222.

The Census protocols 230 can proceed to the Medical Director Reports protocols 240 by step 214, which is coupled by connection 228 to the Physician Data database 292 located in the HNI Connect DataStore 275. The Medical Director Reports protocols 230 can also proceed to the Administration/Medical Officer protocols 270 by step 226, which is coupled by connection 227 to the HNI Connect Knowledge Data database 283 located in the HNI Connect DataStore 275. The Physician Data database 292 is coupled to the HNI Connect Knowledge Data database 283 by connection 229, and the HNI Connect Knowledge Data database 283 is connected to the Hospital Data database 277 by connection 231.

The Census protocols 230 allow the User to access Provider/User Census 260 information, Group Census 295 information, or Bi-directional Transfer 293 information. Further, the computer control software supports the admission and discharge of patients using the Quick Entry protocols 220, including the ability to transfer patients to other facilities and the care of other physicians. When a User wishes to transfer a patient's care to another physician, the Bi-Directional Transfer 293 protocols or the Quick Entry 220 protocols may be used. After User Login, the User chooses the patient being transferred and puts in a description of why the transfer is occurring, the status of the patient, the identification of the new physician, hospitalist, or facility where the patient is being transferred to. The information relating to the patient transfer may be accessed from, or input into, the computer system using a desktop computer, mobile phone, intelligent pad devices, or other personal communication device, and the physician, hospitalist, or User that is having the patient transferred to him or her will receive an email, text message or other notification about the transfer in patient care to him or her. That doctor, physician or hospitalist will be added to the User's having rights and privileges to that particular patient's information.

The databases 292, 283 and 277 in the HNI Connect Datastore 275 are coupled to the HNI Operations protocols 294, which include the Physicians protocols 291 connected by connection 299 to the HNI Analytics protocols 296, which is connected by connection 298 to the Administrative Reports protocols 297.

Figure 3:
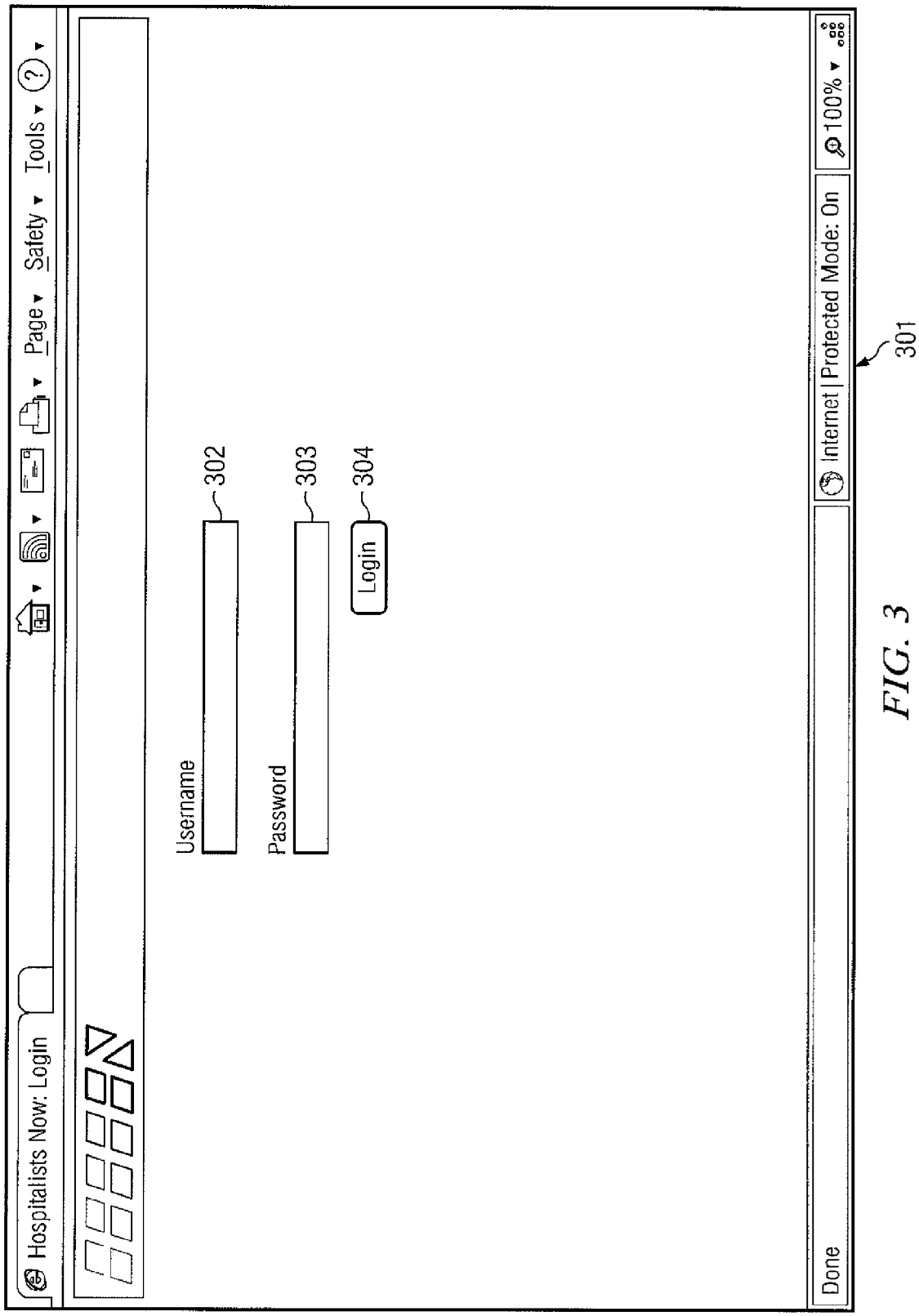
FIG. 3 shows an example of HNI Connect Login page.

As shown in FIG. 3, a user can enter his or her personal username 302 and password 304 (User@hospitalistsnow.com and password) through the HIPAA compliant interface 301. After entry of the username 302 and password 303, the user activates the interface by electronically pressing or triggering the Login button 304. The user accesses the system through a role-based security model, and users are uniquely authenticated based on role, function, location and facility.

Figure 4:
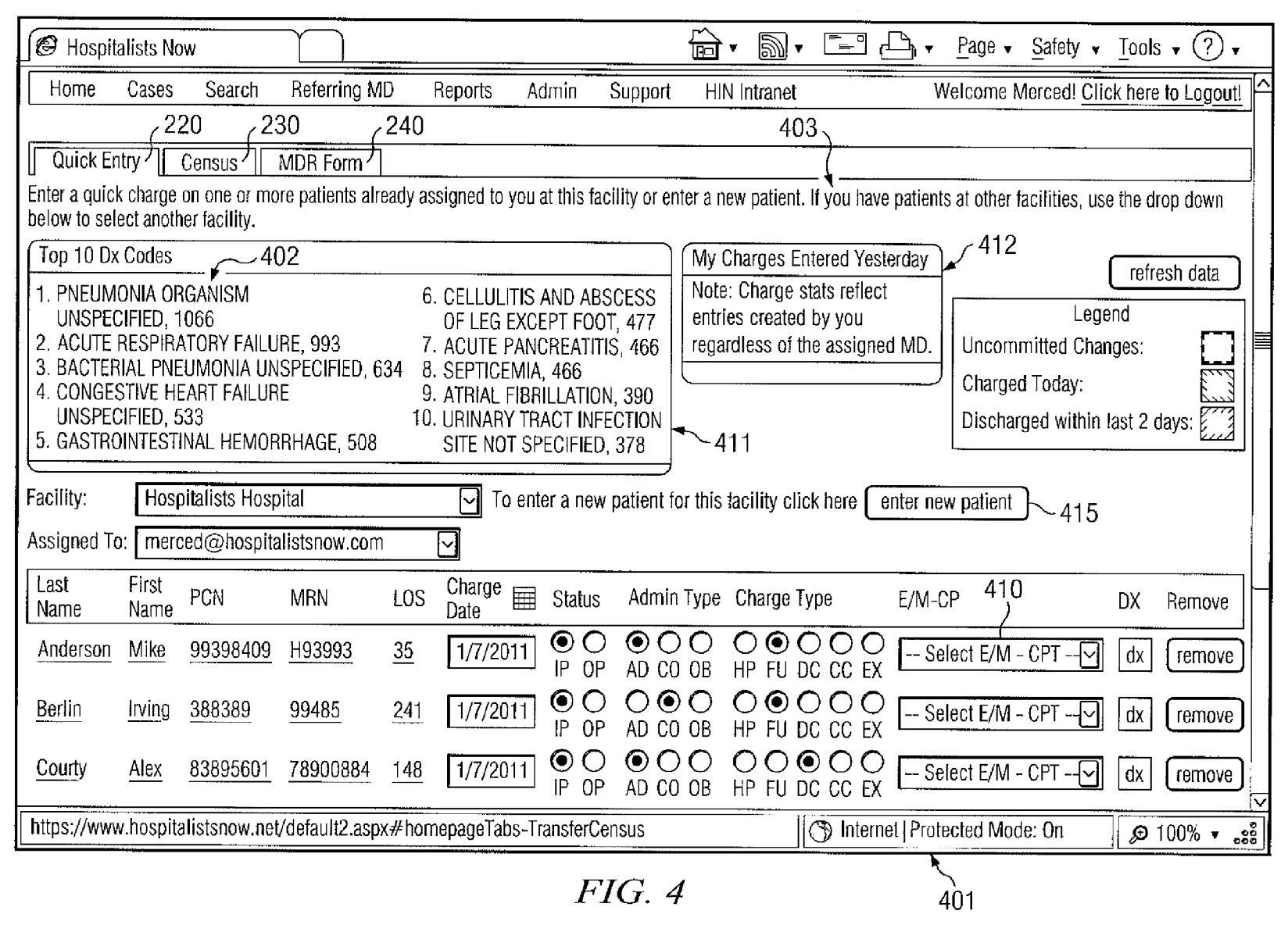

As shown in FIG. 4, the invention has a data audit procedure website 401 where pre-defined data fields are addressed to determine the availability, accountability, and location of responsibility within the user login. Once a user's information is defined, data sources are analyzed and user personalization is generated. This process provides each credentialed user a tailored, detailed view of their work list, census, and charges.

After successfully logging in, the data capture solutions and reporting architecture enables users to have a standard view of a "to-date" diagnosis for standard codes 402, charge and diagnosis history of an individual patient or a group of patients. The architecture is designed to be flexible and tailored to each user. The tabs at the top of webpage 401 correspond to the Census protocols 230, Charge Capture-Quick Entry protocols 220, and the Medical Director Reports protocols 240. As shown at 403, the user may be assigned to or be able to view one or multiple facilities and be presented with a drop down menu allowing them parse data specific to facility or group.

Another function provided in website 401 is an up-to-date and concise view of the past week's productivity. The invention empowers users to see a rolling week and daily tally and description of all Evaluation and Management (E&M) codes 410 detailing the physician's levels of care. Data is captured real time and reported in real time or in time sequence. Once data is captured, this data is then entered archived in HNI Connect's data warehouse 110 to allow for business intelligence tailoring, performance modeling and dashboard reporting.

Data is captured using the protocols at 411, which include facility designation, assigned/responsible physician for care 403, and the ability to manually create a record 412 if required. In one embodiment, focused on E&M Codes 410, the invention supports the reliable and consistent method for capturing the service and clinical duties of the hospitalist has been developed in the hospitalist Quick Entry (QE) grid shown in 401. Any patient who has received a level of care must be documented and captured quickly and accurately, and new patient information is entered through the new patient data entry 415. The QE system comprises a method and option for the assigned physician to capture and document the care provided.

Figure 5:
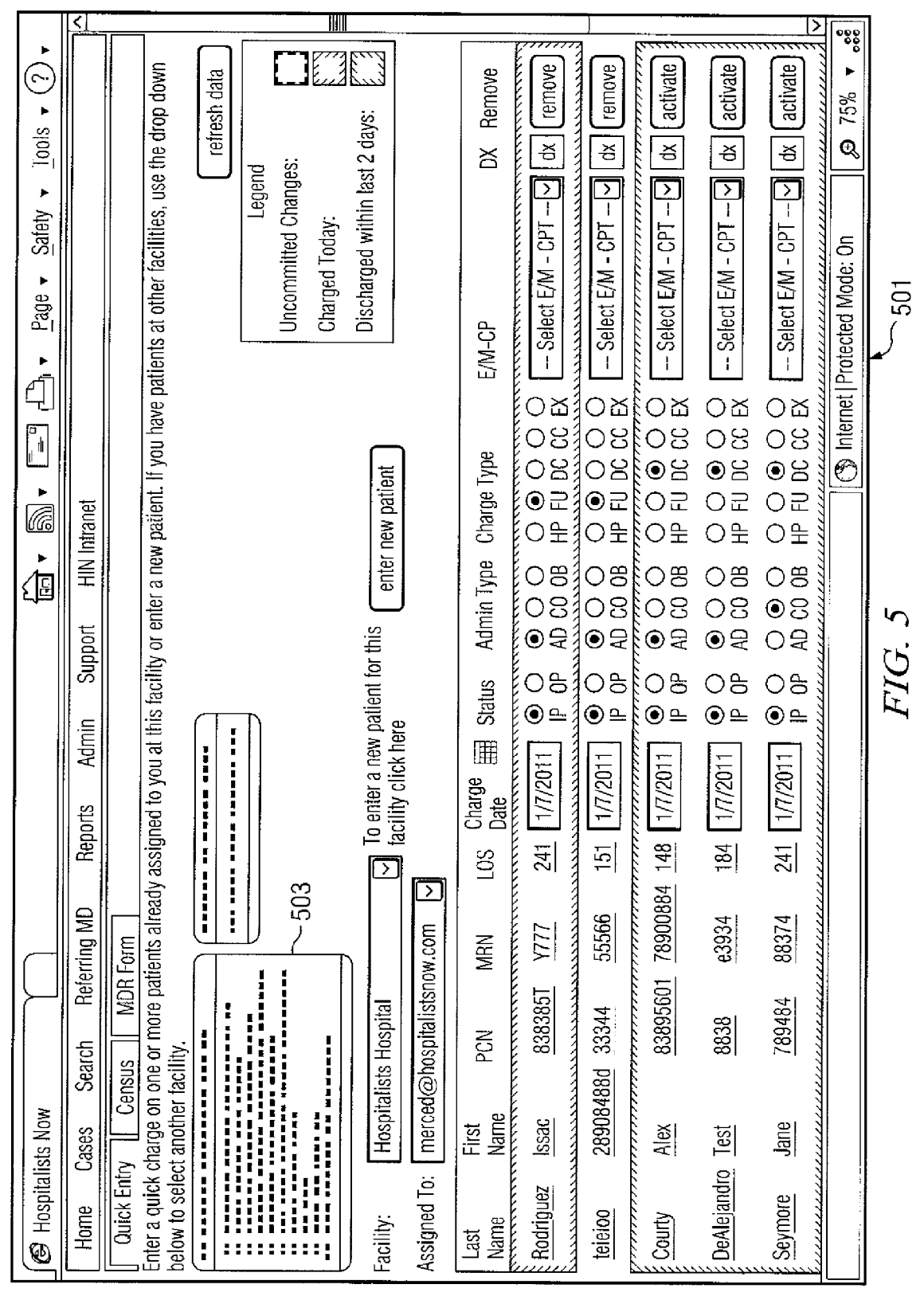

As shown in FIG. 5, data is captured on webpage 501 by either direct data integration with a hospitals' EMR or HIS systems or via manual entry. The types of data that can be entered consist of basic patient demographics including (but not limited to) patient name, assigned facility, patient number, medical record or chart number, and a running calculation within the application of the length of stay (LOS).

This Quick Entry QE grid on page 501 enables hospitalist medicine providers to capture all major data related to their performance and duties. These include documentation of patient progress, diagnosis, coding for physician group and facility/hospital, as well as: Date of Service, Status type=Inpatient or Outpatient, Admit Type=Admission, Consult, or Observation, Charge type=History and Physical (HP), Progress Note (FU), Discharge (DC), Critical Care (CC), Extended/Prolonged Care Code (EX). In addition, this standard Quick Entry QE form 501 provides reminders and coding logic to assist them in proper charge capture. Once the data is submitted, the data is reported on and provided to necessary personnel for business cost accounting, billing, and administrative review of performance in the HNI Connect Datastore 275. Also, data entered is stored in HNI Connect's data warehouse 110 for business intelligence tailoring, performance modeling and dashboard reporting.

This Quick Entry QE grid on page 501 also offers providers a simplified method for capturing one or many diagnosis codes (DX) 503. The DX codes 503 are standardized and by definition are the International Statistical Classification of Diseases and Related Health Problems (most commonly known as "ICD"). The International Classification of Diseases is published by the World Health Organization (WHO). The application automatically provides the currently released ICD-9 codes. ICD-9s are the International Classification of Diseases, Clinical Modification (ICD-9-CM) and are classified using assigned codes to identify diagnoses associated with inpatient, outpatient, and physician office utilization in the U.S. The ICD-9-CM is based on the ICD-9 but provides for additional morbidity detail and is annually updated on a predetermined date.

In another embodiment, the physician's most recent diagnosis will prepopulate in the diagnosis window 501 drop down menu. The hospitalist provider is simply required to begin typing either the first few letters of the diagnosis or the DX code itself, and the application will auto populate the string. The application incorporates a method to provide the user with relevant DX codes, which are numeric codes corresponding to a particular diagnosis. The software application can analyze and account for the physician frequency of use of a diagnosis or DX code, facility frequency of use of a diagnosis or DX code, along with other methods to provide a tailored and accurate listing for the user. The list or analysis results can be sorted in order of relevance or frequency of use by physician or by facility. Primary diagnosis and DX codes can be listed and recorded, with second, third, fourth and fifth diagnosis codes also being listed.

By analyzing the frequency of use of a diagnosis or DX code by physician or facility, the software program can provide alerts as to possible contagious infections, diseases or maladies to which the proper authorities (e.g. Center of Disease Control) need to be notified. Also, if there is no system or population rise in a particular diagnosis, the facility can be alerted by the software program of a particular infectious situation in their facility. For a particular physician, an overuse of a particular diagnosis or DX code can alert the facility or physician as to an inappropriate tendency to rely on a diagnosis more than other diagnosis or DX codes, or the opposite that certain diagnosis or DX codes are used too infrequently. However it is noted that all DX options are available to the user. This analysis offers significant time savings to the end user. A user-friendly experience is provided, while accumulating valuable diagnosis and trending information.

The page 501 also provides the user with the option of quickly removing a user record if the record needs to be quickly removed. Administration and auditing will receive notification of any record removed. Even though the removal is provided for by the website 501, the data is submitted and reported through the system.

FIG. 6 shows the website entries on webpage 601 for the creation and completion of a new patient encounter and Direct Data entry into the software application. This option allows the provider the ability to quickly enter a patient encounter into the application directly with the minimal data elements required to report clinical services and charges. The last name 603 provides for immediate association and linkage of patient encounter to proper Assigned MD/Provider, and the present invention requires the hospitalist to capture the identification of the referring physician. Once the form is completed, the data is aggregated then complied into a physician directory database. Data captured is again entered into the analytic portion of the system for business intelligence development, performance modeling and dashboard reporting. Data is also captured on page 601 such as the working ICD9 or primary diagnosis for the encounter and service level 606.

As shown in FIG. 7, the invention supports the importation of direct data from Electronic Medical Records or Hospital Information Systems (EMR/HIS) into system software application programs using the Census 230 tab. The hospital provider has options to complete documentation in Quick Entry (QE) grid websites (FIGS. 4 to 6) or in the specially designed and detailed Cases section of the application.

This Census view webpage 701 gives the hospitalist provider a management tool for census management and transfer of care. This page 701 using the Census 230 tab facilitates proper and accountable patient care. In this embodiment, the assigned provider's Census 230 is clearly provided from direct data entry or data importation from EMR/HIS systems. The software provides real-time feedback to hospitalist provider on their performance as well as hospital benchmarking.

In FIG. 7, webpage 701 supports the appropriate and designed functions for the hospitalist provider in managing facility coverage. Oftentimes, the hospitalist may be managing census populations from varying facilities, but the invention supports a web-enabled application designed to provide a consistent methods for managing multiple census populations.

The Census 230 application shown on webpage 701 offers the provider the ability to communicate with facility specific group members and communicate the transfer of patient care 705. The webpage 701 provides concise and critical data along a secure communication link for sharing and confirmation with the parties involved with the patient transfer. Communication and confirmation is noted in the software application, audited, tracked and reported. Communication of file information is provided via a secure password protected, HIPAA compliant, encrypted PDF communication link.

The Census 230 application shown in webpage 701 also supports the development of a group's census information, which can be pre-populated into the system via direct data access from the hospital information systems provided to the hospitalist provider. Once the appropriate patient records have been identified, a hospitalist provider may transfer patient records to his/her census to take ownership and responsibility of the patient care. A user may directly transfer the record and the group member may provide permission for the record. Communication and confirmation is noted in the software application, audited, tracked and reported, and communication is provided via a secure password protected, HIPAA compliant, encrypted PDF communication link.

FIG. 8 shows the Medical Data Records tab 240 activated in page 801, which provides a communication tool between the hospitalist medical director of a facility or group to the chief medical director and/or any other significant administrative personnel. Upon completion of the form shown on page 801, the hospitalist provider will offer detailed information about the facility. Specific highlights, items in progress, group and facility successes and challenges are detailed on entry locations 805 on webpage 801.

The medical director report (MDR) webpage 801 is provided at regular intervals and scheduling with reminders being provided to user in the user setup profile. AS shown on webpage 801, the MDR records may be completed in one session, or temporarily suspended with an incomplete MDR record saved as a draft—the draft record being completed at a later date. Upon successful completion and submission of the MDR record 801, the communication and confirmation is noted within the software application, audited, tracked and reported. The MDR 801 communication is provided to key personnel in a group or "team" as determined in the user profile, and is transmitted via a secure password protected, HIPAA compliant, encrypted PDF communication link to those group members. The HNI Connect application aggregates needed information from the report, applies data to an HNI Connect form template, encrypts the communication using 128 bit AES encryption algorithm, then is transferred using the SMTP transfer method protocol. The MDR 240 information input on webpage 801 can be used for hospitalist physician reviews, hospitalist/facility meetings, and physician performance and productivity evaluations.

Figure 9:
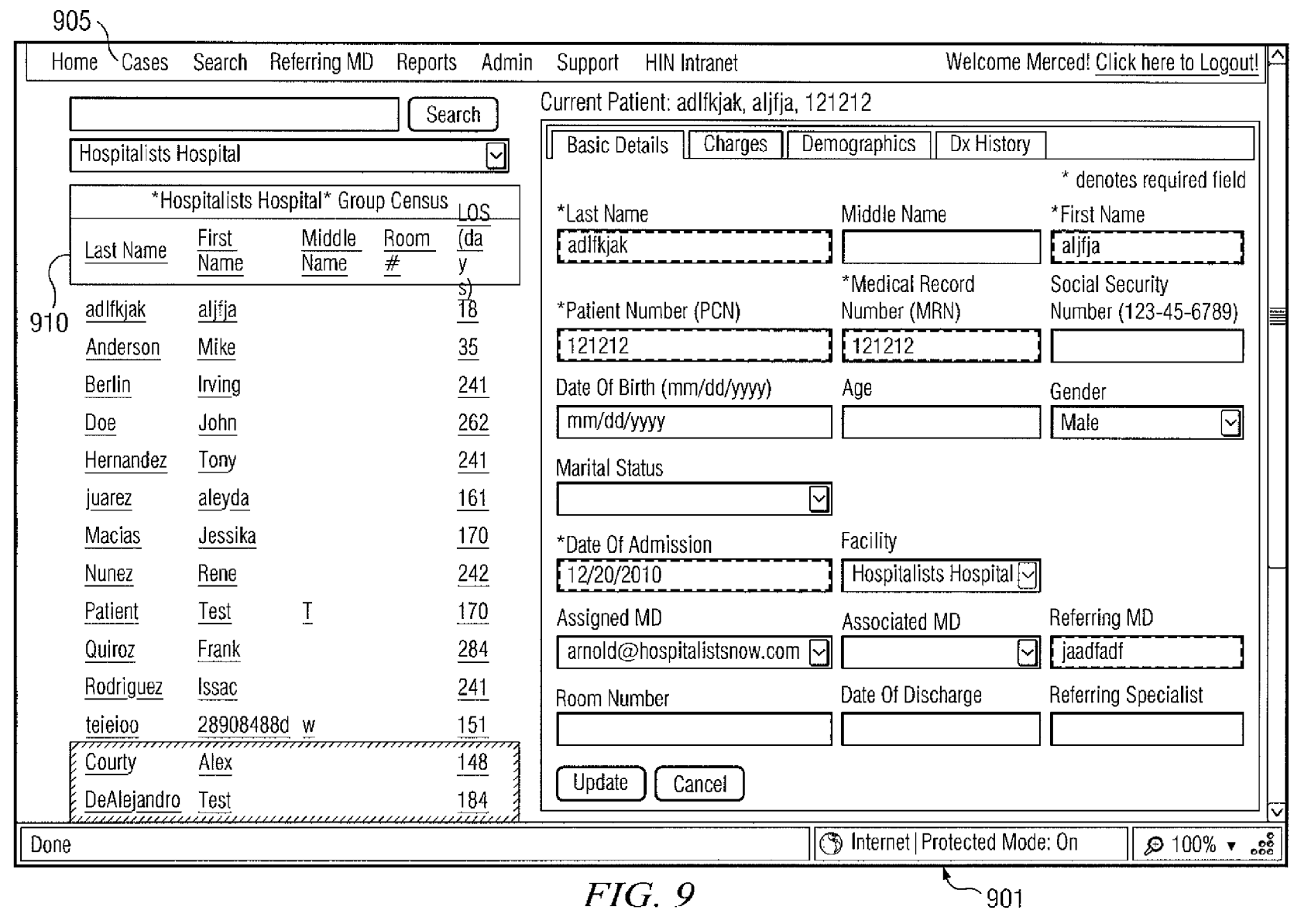

FIG. 9 shows the Cases tab 905 activated on webpage 901, which allows the hospitalist providers to access stored information and an acquired knowledge accrued in the development process. Upon successful navigation of the webpage 901, the cases tab 905 window offers the hospitalist provider with detailed information of the facility and group census, as-well-as direct access to aggregated and stored patient information. With the Cases webpage 901, the user has the ability to choose from an assortment of patients and facilities dependent upon the user's permission and role definition.

On webpage 901, the user is provided the ability to search directly for patient records using any portion of a patient name. In this embodiment, once a record is selected, all patient record data collected will be provided to hospitalist service provider on the listing 910 shown on left side of webpage 905. In this embodiment of webpage 901, the invention is designed to support the stored information and the workflow that both hospitalist physicians and their associated Non-Physician Providers (NPP) need to manage census and rounding information. This webpage 901 assists in workflow management and ensures documentation and proper charge compliance.

In FIG. 9, the cases 905 webpage screen 901 provides a quick view and access on listing 910 to both active patients in current census, patients seen within the past 30 days, and highlights patients discharged within the past 48 hours. Details provided are Patient Name, Admit date, LOS, patient age, marital status, facility name, assigned MD, associated MD, referring MD, referring specialist, room number, and date of discharge if discharged. On webpage 905, patients that have been discharged within the past 48 hours are highlighted red and kept in the physician's active census. If patients are re-admitted within that period of time, this functionality provides the hospitalist with the flexibility to update and correct discharge information as needed. It also provides re-admission information, and this data is collected, audited and reported to the databases maintained by the invention.

Figure 10:
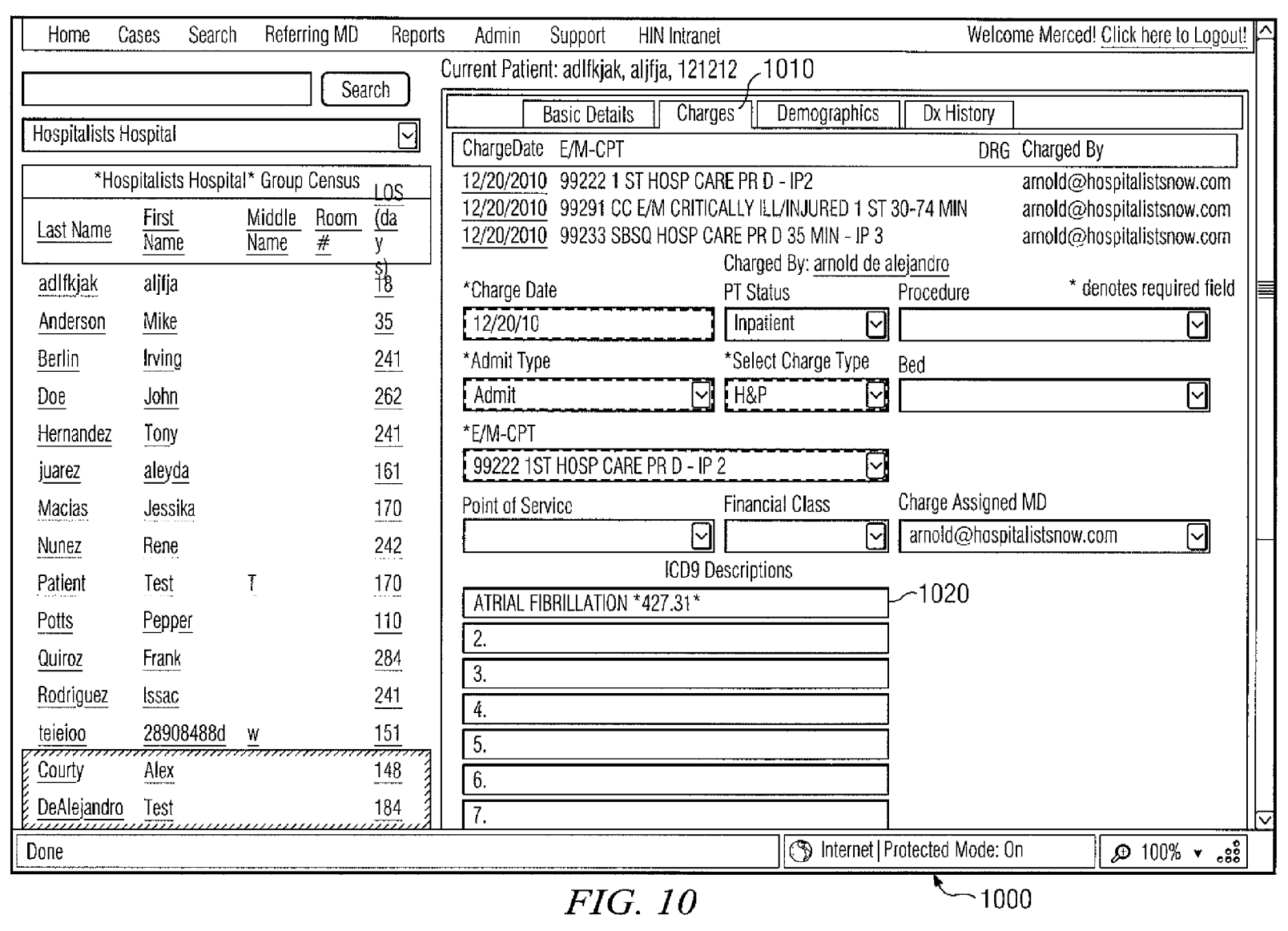

On FIG. 10, webpage 1000 supports the input of appropriate information to calculate appropriate charge information for both the hospitalist physician and his associated group and NPPs. Once the charges screen tab 1010 is activated, the system provides a charge history and details. The records are based upon the chart/medical record and particular patient # and visit ID. The charge dates are given along with the assigned physician to the charge. The charge date, Patient type, patient status, procedure codes, notes, point of service, and financial class information can be provided on webpage 1000 for FIG. 10.

On webpage 1000, the physician is provided the ability to see the diagnosis codes and diagnosis history 1020 from the group physicians as well. The hospitalist provider has the flexibility and end-user permission to edit his charge and update and edit any associated charge on webpage 1020. This data is recorded and any updates are audited and reported to key executive and clinical staff via secure, encrypted pdf communication link.

Figure 11:
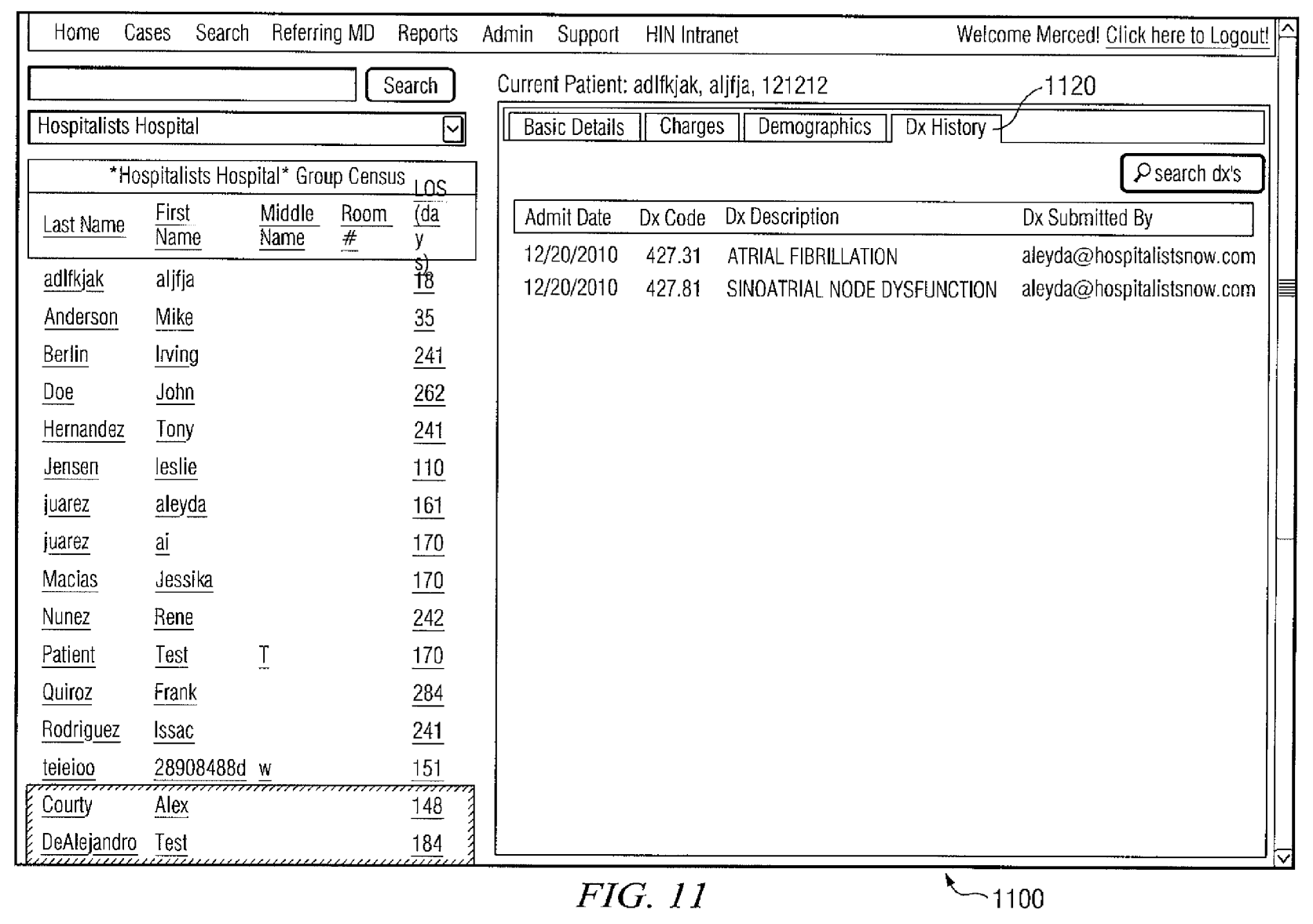

In FIG. 11, the webpage 1100 on the present invention supports the capture, analysis and historical recording and presentation of the patient encounter when the Dx History 1120 button is activated. This Dx History 1120 solution integrates a variety of clinical data repositories including the ICD9 and ICD10 codes, laboratory data, pharmacy data, medical diagnosis data, diagnostic related group data (DRG) data, direct charge data entered by hospitalist provider and/or associated NPP. The data shown on this webpage 1120 is provided to the system then algorithmically analyzed, and in an alternative embodiment, the invention supports the compilation and providing of all available data to any direct provider input in order to minimize the time and effort required for data entry by the hospitalist provider and/or associated NPP.

Figure 12:
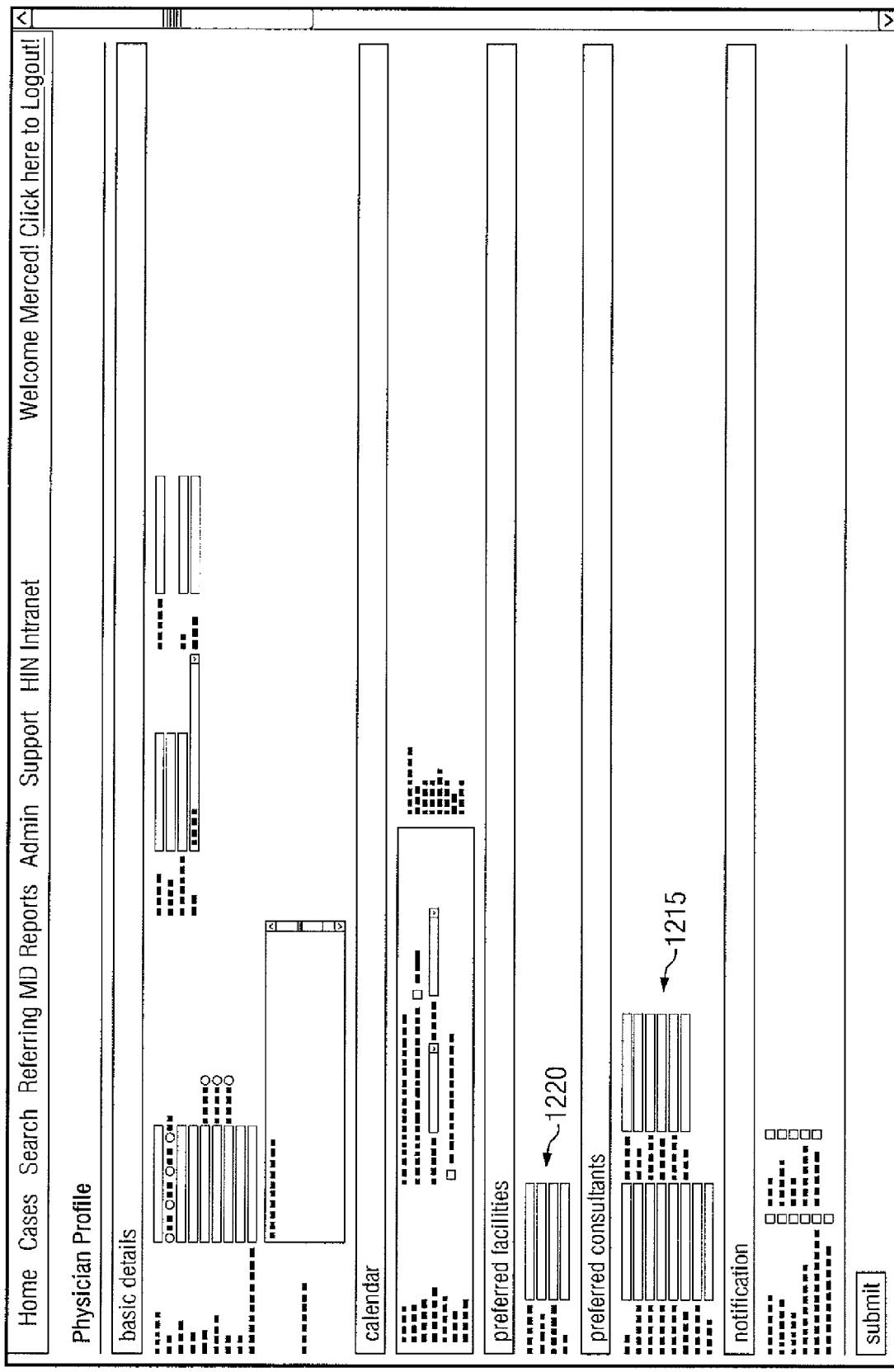
FIG. 12 shows the constructs of the referring MD (Primary Care Physician—PCP) portal.

In FIG. 12, webpage 1200 is presented as a referring physician profile input form and physician data directory. On this webpage 1200, physician data is captured and assigned to patient records, and this information provides valuable referral feedback to the attending hospitalist provider, hospital/facility of service, administration and referring physician himself. Not only is referral data provided, but clinical data is aggregated and analyzed by physician and/or diagnosis. The invention collects automated inputs, combines these automated inputs with referral and clinical data, referring physician and nurse data, credentialed facilities, preferred facilities, preferred consultants, feedback and communication preferences and provides multiple secure communication methods. All this data is submitted into the analytic portion of the solution and is warehoused for performance modeling in the database warehouse 110 for future use in the dashboard reporting, business analytics, and accounting.

On webpage 1200, referring physician demographic and basic information are recorded and kept for future analysis. Fields included for referring physician information include name, title, medical specialty, address, license number, national provider identifier (NPI), contact information, cell phone, and business phone, preferred method of contact, fax number, email address, main nursing contact and privileged facilities.

In this embodiment shown on FIG. 12, a calendar with an associated schedule for referring physician is provided. Users will be offered the ability to automate provider schedules, and these schedules are stored and archived for future analysis and communication.

The physician profile form on webpage 1200 also provides a method for capturing the referring physicians preferred discharge facilities. Examples of such discharge facilities 1220 such as preferred nursing homes, preferred home health organizations, preferred rehabilitation facilities, and/or preferred long term assisted care hospitals (LTACH). The information input into and provided on webpage 1200 is provided prior to any direct provider input in order to minimize the time and effort required for data entry by the hospitalist provider and/or associated NPP.

In the embodiment of the invention shown on FIG. 12, the method for input of preferred consultants is shown on webpage 1200. Once captured, the information is provided to the hospitalist provider in order to minimize the time required for data entry and manual communication to both the referring physician and his associated preferred consultants. Preferred consultant data input fields 1215 includes GI, Pulmonary, Neurology, Urology, Psychiatry, General Surgery, Cardiology, Cardio Vascular Surgery, Oncology, Orthopedics, Nephrology, Podiatry, OBS/Gynecology.

The physician profile capture form on webpage 1200 also provides methods for preferred types of communication with a physician, and supports future automation of notifications to a physician. For example, if a referring physician prefers to be notified on each admission, the software application on webpage 1200 provides the means and method to securely communicate with the referring physician.

Examples of types of communications include notifications for all admissions, all discharges, all deaths, changes in code status, transfer to Nursing Home (NH), LTACH or REHAB. The HNI Connect application provides the form and method to capture the referring MD's notification preferences. Those preferences are gathered by direct communication with the referring MD. Those preferences are recorded in the PCP profile form. The Notifications are triggered by once the referring MD is identified by the users. All subsequent communication to that referring MD is now associated with that profile. Going forward the referring MD's patient data is transmitted via a secure password protected, HIPAA compliant encrypted PDF communication link to that referring MD. The HNI Connect application aggregates needed information from the patient encounter, applies data to HNI connect template, encrypts the communication using 128 bit AES encryption algorithm, then is transferred using the SMTP transfer method protocol. Additional notifications include discharges to Home Health, notification of strokes, amputations, surgery, ICU admission, and initiation of hemodialysis (HD). The information input into webpage 1200 is provided prior to any direct provider input in order to minimize the time and effort required for data entry by the hospitalist provider and/or associated NPP. The data is submitted into the analytic portion of software application solution and is warehoused, provided for performance modeling, called back for reporting dashboards, and used for business analytics and financial reporting and accounting.

As shown in FIG. 13, the invention supports an asp.net web software application, which allows the system to support the flexible reporting capabilities. On webpage 1300, data is collected and input into the system, and that data can be reported against and parameters such as dates of service, dates of charges, facilities of service, multiple facilities, and multiple providers. On webpage 1300, a SEQUEL (SQL) reporting server is dedicated and assigned to aggregate, report and provide valuable real-time feedback to the hospitalist provider, NPP and administrative staff for analysis. Examples of current reports include CPT utilization, CPT Breakdown, RVU tally and totals, RVU performance, Charges, Levels of EM reporting. Data export mechanism provided but not limited to printable reports, XML, TXT, CSV, PDF, or MS EXCEL.

In FIG. 14, the asp.net software application webpage 1400 provides an improved format, substance, and calculation of a Patient Satisfaction Survey Database. FIG. 14 reflects the starting point of the improved survey census analysis, but the creation of the survey is adjustable given the method assigned via role based method. On webpage 1400, the application is designed to save the administrator time by providing a means to quickly select most recently discharged patients (discharged within 48 hours), then offer the ability to generate a onetime login code to the patient to participate in the survey. A nurse, NPP, hospitalist provider, or any approved user will be afforded access to the survey generated pages. Once the survey questionnaire is generated, the unique one-time login must be used within 14 days or survey will automatically expire. The HNI Connect application aggregates needed information from the questionnaire form, applies data to HNI Connect notification template, encrypts the communication using 128 bit AES encryption algorithm, then transfers the data using the SMTP transfer method protocol. Data is collected and submitted into the analytic portion of solution and is warehoused for performance modeling, dashboard reporting, business analytics, and accounting.

As shown on FIG. 15, the invention supports an administrative portal webpage 1500 that is used for adjustable and tailored questionnaire generation. Using webpage 1500, approved users will be provided access to manage questions, assign questions to a service and admission type. And, webpage 1500 provides for categorization 1510 and issuance of immediate feedback 1505 of questionnaire and its contents to the user with the newly generated questions readily seen below the generation tool. The system identifies the questions generated by listing them and assigning them to a type, whether the question is a General/Program/Hospital question 1510. A category 1510 is also provided. Categories 1510 include Admit H&P, Follow-up PN, Discharge, Critical Care, Extended/Prolonged care, Core Measure, Procedure, and others as needed. If one or more questions are created, they will all be provided and immediately confirmed on-screen for the user.

FIG. 16 shows performance metrics on webpage 1600 for the hospitalist provider performance. On webpage 1600, hospitalist provider, physician, physician group or facility performance is provided, and can be shown versus a metric benchmark for analysis of the physician, hospitalist, group or facility performance. These persons, groups or facilities are benchmarked with various graphical depictions based on collected data in the system. The information disclosed in this graphical manner can include physician name, physician number, patient record/medical number, patient visit, diagnosis related group identification information, diagnosis description, diagnosis weighting, as well as charging, financial, payment information, financial class of patients, and how long the patient has been in the facility. These graphical depictions are provided both in a set of standard or "canned" reports and have the flexibility to generate adjustable reports based upon submitted and amassed data.

The user may view one or all in a set prepared for presentation shown on webpage 1500. A data export mechanism is provided to allow printable reports via XML, TXT, CSV, PDF, or MS EXCEL. The Reporting mechanism allows the user to choose a highly detailed view of credentialed facility data or summary reports as desired. Examples include hospitalist cases average length of stay (ALOS) 1603 vs. geometric mean length of stay (GMLOS) 1605 with corresponding case mix index (CMI), hospitalist cases vs. non-hospitalist cases with corresponding variances ALOS vs. GMLOS reflecting CMI, hospitalist six (6) month trending analysis 1610, top ten cases with detail DRG description reflecting variances and CMI 1620. Once again, data is archived into the analytic portion of solution, archived for future trending analysis, aggregated for performance modeling, historical reporting dashboards, and used for business analytics and accounting.

FIG. 17 shows the physician satisfaction report and results example for webpage 1700. Ratings are provided for survey questions on the ratings scale provided on the left hand side of webpage 1700. FIG. 18 reflects a core measure (CM) webpage 1800 that supports the application of core measurements for a patient tracking and notification system. The present invention notifies the hospitalist provider in real time when a core measure diagnosis is designated and desired, and a core measure capture form is provided to the hospitalist provider with data elements required by the facility to be submitted to The Center for Medicare and Medicaid Services (CMS) and/or the Joint Commission for the Accreditation of Hospitals (JCAHO).

The hospitalist provider is given the opportunity in real time to document preferred treatment options for the circumstance. Core measurement CM data 1805 captured on webpage 1800 includes the AMI core measure, HF core measure, Pneumonia (CAP) CM, H&K CM, CABG Coronary Artery Bypass Graft Measure, and SCIP CM. Upon submission, data is transferred to the analytic portion of the solution. A secure, encrypted, HIPAA compliant notification is sent to the hospitalist care provider with the form results. An encrypted message is also provided to key facility personal such as case management and clinical and/or administrative directors. Case Management personnel are put in a group or "team" as determined in the user profile. The Core Measure communication is transmitted via a secure password protected, HIPAA compliant, encrypted PDF communication link to those group members. The HNI Connect application aggregates needed information from the measure form, applies data to HNI Connect template, encrypts the communication using 128 bit AES encryption algorithm, then transfers the data using the SMTP transfer method protocol. This secure communication provides highly valuable information for both the provider and facility. As an additional benefit, the embodiment of this invention also comprises an easy to use, electronic platform to collect this clinical information to enhance the partner facilities medical records.

This information captured on webpage 1800 assists the partnered facilities by improving compliance by providing relevant information to key players as opposed to assigning valuable resources to track down this data. The information captured on webpage 1800 is also archived into our analytic portion of the software solution for improved benchmark reporting, and the collection and compliance of these measures may offer financial enhancements to participating facilities from CMS thus increasing the hospitalist service value.

FIG. 19 shows a mobile interface and platform webpage 1900. This webpage 1900 supports software developed and created to integrate critical hospitalist user data into the system. The system provides a web-based, SSL encrypted platform 1900 for the direct entry of healthcare related data from any secure location. The system is developed for use on a variety of hardware devices. These devices include portable cellular smartphones with a secure web interface such as the iPhone, Android, and Blackberry RIM devices, tablet computing devices such as table PCs, Android Tablets, as well as the Apple iPad and can be integrated to gather data directly from various hospital information systems (HIS). The software used in the invention is adaptable to accommodate the changing portable web environments.

In order to provide the hospitalist provider with access to their credentialed facility, a mobile patient search and facility lookup option 1910 is provided to place the user in his credentialed and desired facility of choice. Once a mobile device authenticates the user or facility, the user is provided a quick view 1920 of the active patients in their census. A simple point/click to the desired patient record is required to facilitate quick charge entry from this mobile platform, and the data fields provided for that patient include patient name, room # or location, and active length of stay (LOS).

As shown in FIG. 20, after the desired record is chosen from the active mobile census, relevant clinical, historical and charge information is provided to the user as displayed on webpage 2000. Logic is developed in the application to reflect the last entered charge data, which is prepopulated to minimize key strokes for the user. Should a simple follow-up charge need be created, the user will verify information, confirm date, previous diagnosis, and submit the charge, and data on webpage 2000 is added to the analytic database for charge creation and relevant personnel for management.

Historical charge information is provided to the user on webpage 2000 via a quick link along with the patient record. Critical charge information is captured and provided on webpage 2000, and the records last active charge is prepopulated to save the user from additional data entry. Once all data is confirmed, the charge may be submitted using the Submit button on webpage 2000. Once the data is submitted, the data is reported to necessary personnel for business cost accounting, billing, and administrative review of performance. Data captured on webpage 2000 is entered into the analytic portion of the system for business intelligence development, performance modeling and dashboard reporting.

Confirmation of the charge's assigned physician is provided on webpage 2000. The ability to quickly edit and add additional diagnosis using the patient record is also provided in the mobile platform in FIG. 20.

While preferred embodiment of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

The invention claimed is:

1. A system for analyzing and displaying performance metrics and information of a hospitalist at a health care facility comprising:
   a computer management system having a computer processor, input/output devices, subprograms for operation of the computer processor, a data buffer, and one or more input/output ports for receipt and transmission of patient data, hospitalist information, and administration messages and information, said computer management system provides real-time demographic, financial, clinical, and patient data for each hospitalist for display to a hospitalist user and a health care facility administrative user;
   a statistical subprogram operating on the computer management system computer processor, said statistical subprogram coupled to a primary database on the computer management system, said primary database maintaining compiled demographic, financial, clinical, and patient data for each patient admitted to the health care facility and each hospitalist that works at the health care facility in addition to geometric length of stay data,
      said statistical subprogram calculating the average length of stay for one or more patients assigned to one or more hospitalists working at the health care facility by summing the total number of days in the length of stay for said one or more patients and dividing that summation of the total number of days in the length of stay by the number of the one or more patients,
      said statistical subprogram calculating a variance factor by subtracting the average length of stay calculated by the statistical subprogram from the geometric mean length of stay data, said geometric mean length of stay is an average length of stay for a patient representing a benchmark metric performance standard for patient care that can be compared against the average length of stay,
      said computer management system archiving the calculated average length of stay for patients assigned to one or more hospitalists, said geometric mean length of stay data, and said variance factor,
   said computer management system provides a visual graphical comparison of the performance of the hospitalists versus the benchmark metric performance including a first graphical representation of average length of stay and a second graphical representation of the geometric length of stay, said computer management system provides the ability to view the visual graphical comparisons of the first and second graphical representations show the performance of one or more hospitalist versus a geometric mean performance and shows a variance factor showing the variation of the performance of one or more hospitalists versus the mean performance through the input/output port of the computer management system,
   said statistical subprogram archiving and making available to one or more hospitalists or heath care facility administrators data regarding the dosage and type of medication prescribed to one or more patients admitted to the hospital facility and the frequency of a particular diagnosis given to patients by the hospitalists, said hospitalist or said health care facility administrative user receiving a notification if the frequency of a particular diagnosis or frequency of a prescribed medication exceeds a predetermined level, said statistical subprogram providing real-time feedback to hospitalists on their performance as well as health care facility benchmarking, said administration messages and information including diagnosis information for a patient, reports of patient progress, communications and notifications throughout a treatment episode for a patient, and one or more notifications sent to said hospitalist user or said health care facility administrative user.

2. The computer management system of claim 1 for gauging performance of a hospitalist at a health care facility wherein said administration messages include a notification to a physician or hospitalist regarding a patient transfer to that hospitalist.

3. The system of claim 1 for analyzing and displaying performance metrics and information of a hospitalist at a health care facility wherein said one or more patients used to calculate the average length of stay are assigned to one hospitalist.

4. The system of claim 3 for analyzing and displaying performance metrics and information of a hospitalist at a health care facility wherein visual graphical display includes one of the following visual depictions: a speedometer, bar chart, or line graphic chart showing the relative performance of the hospitalist health care professional compared to the metric benchmark performance.

5. The system of claim 1 for analyzing and displaying performance metrics and information of a hospitalist at a health care facility wherein benchmark metric performance involves the number of patients seen by all the hospitalists assigned to a particular hospital facility.

6. The system of claim 5 for analyzing and displaying performance metrics and information of a hospitalist at a health care facility wherein visual graphical display includes one of the following visual depictions: a speedometer, bar chart, or line graphic chart showing the relative performance of the hospitalist compared to the metric benchmark performance.

7. The system of claim 1 for analyzing and displaying performance metrics and information of a hospitalist at a health care facility wherein the hospitalist can examine his or her individual performances to estimate the fees and wages that may be due to him or her for their work at the facility or with the patient.

8. The system of claim 7 for analyzing and displaying performance metrics and information of a hospitalist at a health care facility wherein visual graphical display includes one of the following visual depictions: a speedometer, bar chart, or line graphic chart showing the relative performance of the hospitalist compared to the metric benchmark performance.

9. The system of claim 1 for analyzing and displaying performance metrics and information of a hospitalist at a health care facility wherein the frequency of particular diagnosis given to patient is used to determine if there is contagious infection problem.

10. A system for analyzing and displaying performance metrics and information of a hospitalist at a health care facility comprising:

a computer management system having a computer processor, input/output devices, subprograms for operation of the computer processor, a data buffer, and one or more input/output ports for receipt and transmission of patient data, hospitalist information, and administration messages and information, said computer management system provides real-time demographic, financial, clinical, and patient data for display to a hospitalist user and a health care facility administrative user;

a statistical subprogram operating on the computer management system computer processor, said statistical subprogram coupled to a primary database on the computer management system, said primary database maintaining compiled demographic, financial, clinical, and patient data for each patient admitted to the health care facility and each hospitalist that works at the health care facility in addition to geometric length of stay data, said statistical subprogram calculating the average length of stay for one or more patients assigned to one or more hospitalists working at the health care facility by summing the total number of days in the length of stay for said one or more patients and dividing that summation of the total number of days in the length of stay by the number of the one or more patients, said statistical subprogram calculating a variance factor by subtracting the average length of stay calculated by the statistical subprogram from the geometric mean length of stay data, said geometric mean length of stay is an average length of stay for a patient representing a benchmark metric performance standard for patient care that can be compared against the average length of stay, said computer management system archiving the calculated average length of stay for patients assigned to one or more hospitalists, said geometric mean length of stay data, and said variance factor, said computer management system provides a comparison of the performance of the hospitalists versus the geometric mean length of stay data representing a benchmark metric performance, the computer management system allowing said hospitalists or health care facility administrative users to access the results of the statistical subprogram and views of the visual graphical comparisons of performance of one or more hospitalists versus the geometric mean data stored in the database archive, said hospitalist or said health care facility administrative user receiving a notification if the frequency of a particular diagnosis or frequency of a prescribed medication exceeds a predetermined level, said statistical subprogram of providing real-time feedback to hospitalist or health care facility administrative user on performance as well as health care benchmarking, said administration messages and information including diagnosis information for a patient, reports of patient progress, communications and notifications throughout a treatment episode for a patient, and one or more notifications sent to said hospitalist user or said health care facility administrative user regarding potential contagious infection problems.

11. The system of claim 10 for analyzing and displaying performance metrics and information of a hospitalist at a health care facility wherein said one or more patients used to calculate the average length of stay are assigned to one hospitalist.

12. The system of claim 11 for analyzing and displaying performance metrics and information of a hospitalist at a health care facility wherein visual graphical display includes one of the following visual depictions: a speedometer, bar chart, or line graphic chart showing the relative performance of the hospitalist compared to the metric benchmark performance.

13. The system of claim 10 for analyzing and displaying performance metrics and information of a hospitalist at a health care facility wherein benchmark metric performance involves the number of patients seen by all the hospitalists assigned to a particular hospital facility.

14. The system of claim 13 for analyzing and displaying performance metrics and information of a hospitalist at a health care facility wherein visual graphical display includes one of the following visual depictions: a speedometer, bar chart, or line graphic chart showing the relative performance of the hospitalist compared to the metric benchmark performance.

15. The system of claim 10 for analyzing and displaying performance metrics and information of a hospitalist at a health care facility wherein the hospitalist can examine his or her individual performances to estimate the fees and wages that may be due to him or her for their work at the facility or with the patient.

16. The system of claim 15 for analyzing and displaying performance metrics and information of a hospitalist at a health care facility wherein visual graphical display includes one of the following visual depictions: a speedometer, bar chart, or line graphic chart showing the relative performance of the hospitalist compared to the metric benchmark performance.

17. The system of claim 10 for analyzing and displaying performance metrics and information of a hospitalist at a health care facility wherein the frequency of particular diagnosis given to patient is used to determine if there is contagious infection problem.

18. A method for analyzing and displaying performance metrics and information of a hospitalist at a health care facility using a computer management system comprising the steps of:

providing a computer management system with a computer processor, input/output devices, subprograms for operation of the computer processor, a data buffer, and one or more input/output ports for receipt and transmission of patient data, hospitalist information, and administration messages and information, said computer management system provides real-time demographic, financial, clinical, and patient data for display to a hospitalist user or a health care facility administrative user;

executing a statistical subprogram operating on data archived and maintained on a database associated with the computer management system computer processor, analyzing information archived and maintained on the database with the statistical subprogram including the length of stay for one or more patients assigned to one or more hospitalist assigned to the health care facility, calculating the average length of stay for these patients by summing the length of stay by days for each of one or more patients and dividing that total number of days in the length of stay by the number of patients used in this calculation, identifying with the statistical subprogram a benchmark metric performance standard for patient care, said benchmark metric performance standard being a geometric mean length of stay data in addition to the archived information on the database regarding the dosage and type of medication prescribed to a patient by the hospitalist and the frequency of a particular diagnosis given to patients by the hospitalists, said hospitalist user or said health care facility administrative user, comparing the average length of stay for the one or more hospitalists, which shows the performance of a hospitalist or group of hospitalists at the health care facility, against geometric mean data for length of stay, which is the benchmark metric performance standard, and providing a visual graphical comparison of the performance of the hospitalist by showing the calculated average length of stay for patients assigned to said one or more hospitalists versus the geometric mean length of stay data showing the benchmark metric performance, said computer management system allowing said hospitalist users and health care facility administrative users to access the results of the statistical subprogram and view the visual graphical comparisons of performance, said statistical subprogram capable of providing real-time feedback to hospitalist on their performance as well as health care facility benchmarking, sending administration messages and information including notifications of potential infection problems at the health care facility, diagnosis information for a patient, reports of patient progress, communications and notifications throughout a treatment episode for a patient, and one or more notifications sent to said hospitalist user or said health care facility administrative user.

19. The method of claim 18 for analyzing and displaying performance metrics and information of a hospitalist at a health care facility wherein said one or more patients used to calculate the average length of stay are assigned to one hospitalist.

20. The method of claim 19 for analyzing and displaying performance metrics and information of a hospitalist at a health care facility wherein visual graphical display includes one of the following visual depictions: a speedometer, bar chart, or line graphic chart showing the relative performance of the hospitalist health care professional compared to the metric benchmark performance.

21. The method of claim 18 for analyzing and displaying performance metrics and information of a hospitalist at a health care facility wherein benchmark metric performance involves the number of patients seen by all the hospitalists assigned to a particular hospital facility.

22. The method of claim 21 for analyzing and displaying performance metrics and information of a hospitalist at a health care facility wherein visual graphical display includes one of the following visual depictions: a speedometer, bar chart, or line graphic chart showing the relative performance of the hospitalist health care professional compared to the metric benchmark performance.

23. The method of claim 18 for analyzing and displaying performance metrics and information of a hospitalist at a health care facility wherein the physician or hospitalist can examine his or her individual performances to estimate the fees and wages that may be due to him or her for their work at the facility or with the patient.

24. The method of claim 23 for analyzing and displaying performance metrics and information of a hospitalist at a health care facility wherein visual graphical display includes one of the following visual depictions: a speedometer, bar chart, or line graphic chart showing the relative performance of the hospitalist compared to the metric benchmark performance.

25. The method of claim 18 for analyzing and displaying performance metrics and information of a hospitalist at a health care facility wherein the frequency of particular diagnosis given to patient is used to determine if there is contagious infection problem.

* * * * *